(12) United States Patent
Wondka

(10) Patent No.: US 7,406,966 B2
(45) Date of Patent: Aug. 5, 2008

(54) METHOD AND DEVICE FOR NON-INVASIVE VENTILATION WITH NASAL INTERFACE

(75) Inventor: Anthony D. Wondka, Menlo Park, CA (US)

(73) Assignee: Menlo Lifesciences, LLC, Thousand Oaks, CA (US)

( * ) Notice: Subject to any disclaimer, the term of this patent is extended or adjusted under 35 U.S.C. 154(b) by 248 days.

(21) Appl. No.: 10/922,054

(22) Filed: Aug. 18, 2004

(65) Prior Publication Data

US 2005/0066976 A1    Mar. 31, 2005

Related U.S. Application Data

(60) Provisional application No. 60/495,812, filed on Aug. 18, 2003, provisional application No. 60/511,820, filed on Oct. 14, 2003.

(51) Int. Cl.
*A61M 15/08* (2006.01)
*A61M 16/00* (2006.01)
*A62B 18/02* (2006.01)

(52) U.S. Cl. ............................ 128/207.18; 128/204.18; 128/206.11; 128/207.13; 128/207.17

(58) Field of Classification Search ............ 128/200.24, 128/204.18, 204.21, 206.11, 207.13, 207.17, 128/207.18
See application file for complete search history.

(56) References Cited

U.S. PATENT DOCUMENTS

| | | | |
|---|---|---|---|
| 2,735,432 A * | 2/1956 | Hudson | ................. 128/207.18 |
| 4,273,124 A | 6/1981 | Zimmerman | |
| 4,306,567 A | 12/1981 | Krasner | |
| 4,367,735 A | 1/1983 | Dali | |
| 4,506,666 A | 3/1985 | Durkan | |
| 4,570,631 A | 2/1986 | Durkan | |
| 4,648,398 A * | 3/1987 | Agdanowski et al. | .. 128/207.18 |
| 4,753,233 A | 6/1988 | Grimes | |
| 4,782,832 A | 11/1988 | Trimble et al. | |
| 4,803,981 A | 2/1989 | Vickery | |
| 4,808,160 A | 2/1989 | Timmons et al. | |
| 4,818,320 A * | 4/1989 | Weichselbaum | ............ 156/227 |
| 4,919,128 A | 4/1990 | Kopala et al. | |
| 5,042,478 A | 8/1991 | Kopala et al. | |
| 5,046,491 A * | 9/1991 | Derrick | ................. 128/200.24 |
| 5,140,045 A | 8/1992 | Askanazi et al. | |
| 5,375,593 A * | 12/1994 | Press | ..................... 128/207.18 |

(Continued)

OTHER PUBLICATIONS

Bossi, E., "*Continuous positive airway pressure in the spontaneously breathing newborn by means of bilateral nasal cannulation*", Monatsschr Kinderheilkd, Apr. 1975, 123(4):141-6.

(Continued)

*Primary Examiner*—Justine R. Yu
*Assistant Examiner*—Annette F Dixon
(74) *Attorney, Agent, or Firm*—Michele V. Frank; Patton Boggs LLP

(57) ABSTRACT

A nasal ventilation interface including a pair of tubes configured to deliver a ventilation gas. The tubes are attachable at a first end to a ventilation gas supply hose and engageable at a second end with a person's nostril. A coupler is configured to align the pair of tubes with the person's nostrils, wherein each tube has an absence of pneumatic interconnection with the other tube.

22 Claims, 16 Drawing Sheets

U.S. PATENT DOCUMENTS

| | | | |
|---|---|---|---|
| 5,438,979 A * | 8/1995 | Johnson et al. | 128/207.18 |
| 5,443,075 A | 8/1995 | Holscher | |
| 5,477,852 A * | 12/1995 | Landis et al. | 128/207.18 |
| 5,503,146 A | 4/1996 | Froehlich et al. | |
| 5,533,506 A * | 7/1996 | Wood | 128/207.18 |
| 5,551,419 A | 9/1996 | Froehlich et al. | |
| 5,598,837 A | 2/1997 | Sirianne, Jr. et al. | |
| 5,645,053 A | 7/1997 | Remmers et al. | |
| 5,669,377 A | 9/1997 | Fenn | |
| 5,682,881 A | 11/1997 | Winthrop et al. | |
| 5,826,579 A | 10/1998 | Remmers et al. | |
| 5,921,942 A | 7/1999 | Remmers et al. | |
| 5,954,050 A | 9/1999 | Christopher | |
| 6,120,460 A | 9/2000 | Abreu | |
| 6,123,668 A | 9/2000 | Abreu | |
| 6,224,560 B1 | 5/2001 | Gazula et al. | |
| 6,273,859 B1 | 8/2001 | Remmers et al. | |
| 6,286,508 B1 | 9/2001 | Remmers et al. | |
| 6,298,850 B1 | 10/2001 | Argraves | |
| 6,328,038 B1 | 12/2001 | Kessler et al. | |
| 6,328,753 B1 | 12/2001 | Zammit | |
| 6,332,463 B1 | 12/2001 | Farrugia et al. | |
| 6,357,440 B1 | 3/2002 | Hansen et al. | |
| 6,418,928 B1 | 7/2002 | Bordewick | |
| 6,422,240 B1 | 7/2002 | Levitsky et al. | |
| 6,423,001 B1 | 7/2002 | Abreu | |
| 6,431,172 B1 | 8/2002 | Bordewick | |
| 6,439,234 B1 | 8/2002 | Curti et al. | |
| 6,478,026 B1 * | 11/2002 | Wood | 128/207.18 |
| 6,494,206 B1 | 12/2002 | Bergamaschi et al. | |
| 6,505,623 B1 | 1/2003 | Hansen | |
| 6,530,373 B1 | 3/2003 | Patron et al. | |
| 6,550,478 B2 | 4/2003 | Remmers et al. | |
| 6,561,193 B1 * | 5/2003 | Noble | 128/207.18 |
| 6,564,800 B1 | 5/2003 | Olivares | |
| 6,571,794 B1 | 6/2003 | Hansen | |
| 6,571,798 B1 | 6/2003 | Thornton | |
| 6,595,215 B2 | 7/2003 | Wood | |
| 6,644,305 B2 | 11/2003 | MacRae et al. | |
| 6,668,828 B1 * | 12/2003 | Figley et al. | 128/204.18 |
| 6,679,265 B2 * | 1/2004 | Strickland et al. | 128/207.18 |
| 6,691,707 B1 | 2/2004 | Gunaratnam et al. | |
| 6,752,150 B1 | 6/2004 | Remmers et al. | |
| 6,763,832 B1 * | 7/2004 | Kirsch et al. | 128/207.18 |
| 6,866,041 B2 * | 3/2005 | Hardy et al. | 128/204.18 |
| 2002/0020930 A1 | 2/2002 | Austin et al. | |
| 2002/0043264 A1 | 4/2002 | Wickham et al. | |
| 2002/0046755 A1 | 4/2002 | DeVoss | |
| 2002/0055685 A1 | 5/2002 | Levitsky | |
| 2002/0059935 A1 | 5/2002 | Wood | |
| 2002/0066452 A1 | 6/2002 | Kessler | |
| 2002/0078957 A1 | 6/2002 | Remmers et al. | |
| 2002/0092527 A1 | 7/2002 | Wood | |
| 2002/0112730 A1 | 8/2002 | Dutkiewicz | |
| 2002/0157673 A1 | 10/2002 | Kessler | |
| 2003/0047185 A1 | 3/2003 | Olsen | |
| 2003/0069489 A1 | 4/2003 | Abreu | |
| 2003/0094178 A1 | 5/2003 | McAuley | |
| 2003/0111081 A1 | 6/2003 | Gupta | |
| 2003/0116163 A1 | 6/2003 | Wood | |
| 2003/0121519 A1 | 7/2003 | Estes et al. | |
| 2003/0159697 A1 | 8/2003 | Wallace | |
| 2003/0168067 A1 | 9/2003 | Dougill | |
| 2003/0213488 A1 | 11/2003 | Remmers et al. | |
| 2004/0020493 A1 | 2/2004 | Wood | |
| 2004/0025881 A1 | 2/2004 | Gunaratnam et al. | |
| 2004/0050387 A1 | 3/2004 | Younes | |

OTHER PUBLICATIONS

Mettey, R., "*Nasal cannula, a simple, not very cumbersome, and efficacious means to induce a positive expiratory pressure in neonatology*", Med Trop (Mars). Jan.-Mar. 1985; 45('):87-90.

Sullivan et al., "*Reversal of Obstructive Sleep Apnea by Continuous Positive Airway Pressure Applied Through the Nares*", Lancet, 1981 pp. 862-865.

Sanders, MH., "*CPAP via nasal mask: a treatment for occlusive sleep apnea*", Chest. Jan. 1983; 83(1):144-5.

Bach, JR., "*Intermittent positive pressure ventilation via nasal access in the management of respiratory insufficiency*", Chest Jul. 1987; 92(1):168-70.

Bauer, KL, "*ADAM nasal CPAP circuit adaptation: a case report*", Sleep. Jun. 1991; 14.

Lewis, Ricki, "*Breathless No More, Defeating Adult Sleep Apnea*", (FDA Consumer Magazine Jun. 1992).

Nahmias et al., "*Treatment of the Obstructive Sleep Apnea Syndrome Using a Nasopharyngeal Tube*", Chest, 1994, pp. 1142-1147.

Massie, CA., "*Clinical Outcomes related to interface type in pts with obstructive sleep apnea/hypopnea syndrome who are using CPAP*", Chest 2003, Apr. 123.

International Search Report for PCT/US04/26800, filed Jun. 22, 2006.

* cited by examiner

Section F-F

METHOD AND DEVICE FOR NON-INVASIVE VENTILATION WITH NASAL INTERFACE

CROSS REFERENCE TO RELATED APPLICATIONS

This application claims priority to U.S. Provisional Patent Application No. 60/495,812, filed Aug. 18, 2003, and U.S. Provisional Patent Application No. 60/511,820, filed Oct. 14, 2003, which are incorporated herein by reference in their entirety.

FIELD OF INVENTION

This invention relates to a non-invasive ventilation (NIV) patient interface device which provides a route of air entry into a patient's airway and lung. More particularly, this invention can be applied to Obstructive Sleep Apnea (OSA), a condition where the upper airway obstructs, however the teachings herein are applicable to other respiratory conditions.

BACKGROUND OF THE INVENTION

Non-invasive patient interface devices are used in a variety of medical procedures, such as emergency ventilation, anesthesia delivery and recovery, aerosolized medication delivery, augmentation of natural breathing, supplemental oxygen delivery, mechanical ventilation, weaning from mechanical ventilation and for treating Obstructive Sleep Apnea. In the later case continuous positive airway pressure (CPAP) or continuous variable-level positive airway pressure (VPAP) is delivered through the interface device into the patient's airway during sleep to prevent airway obstruction. OSA is unique to all positive airway pressure (PAP) applications in that the patient is otherwise healthy and the therapy has to be a minimally obtrusive in order to not disrupt the patient while sleeping, whereas in other PAP applications disrupting sleep is of negligible concern. There are three different forms of NIV interface devices; Nasal Interfaces, Oral Interfaces and combined Oral-Nasal Interfaces. Of the Nasal Interface type, there are two categories: Nasal Masks and Nasal Interfaces or Cannulae.

Nasal ventilation interface devices are typically used for supplying supplemental oxygen gas to a person's lung during their natural breathing by placing the tips of the device within the person's nostrils or nares. These devices are constructed of tubing diameters substantially smaller than the diameter of the nostrils since the volumetric demand for the supplemental oxygen is very low (<2 LPM) negating the need for large bore tubes, and since the user must be able to breathe room air around the outside of the interface tubes prongs which are placed in the nostrils.

Oxygen nasal cannulae typically comprise a main base tube positioned horizontally under the nose from which two prongs extend at right angles upward and into the nostrils. With some devices, these prongs are designed to pinch the nostril septum to facilitate retention and sometimes are tilted toward each other at their tips to facilitate pinching.

Typically, if not always, the base tube has a through lumen and the oxygen supply tubing usually attaches to and extends from both sides of this base tube, typically routed around the ears then to the front of the neck to secure the apparatus to the patient. In addition to these oxygen interface tubes, a medical practice has been established to use larger nasal interface tubes that seal the nostrils in order to provide positive airway pressure (PAP) ventilation therapy. The practice is especially common in neonates because of the trauma associated with invasive tracheal intubation.

There are two basic forms of nasal interface tubes; non-sealing nasal interface tubes for supplemental oxygen therapy and sealing nasal interface tubes for PAP ventilation.

Recently special versions of sealing nasal interface tubes have been developed which are intended to improve PAP ventilation; however as shall be explained, these designs have significant deficiencies especially when used in OSA applications.

Agdanowski, U.S. Pat. No. 4,648,398 describes an expandable foam-tipped nasal prong wherein the user compresses the foam for insertion into the nostril then the foam re-expands to contact the nostril wall. The nasal prongs are right angle extensions from a base tube like oxygen therapy interface tubes. The Agdanowski device has two significant deficiencies especially when used in an OSA application: (1) The traditional base tube—right angle prong configuration is inherently resistant to flow because air which is forced into the base tube from both sides collides in the middle of the base tube and the air must make an abrupt directional change into the prongs. Generally, a resistant, turbulent design in an OSA application is undesirable because it causes extra noise (which is irritable to the user and bed partner) and because the user must compensate by increasing the pressure setting (which is less comfortable to the user). Increasing the pressure setting is more demanding on the seals, requiring the device to fit tighter to the user's nose (also less comfortable to the user). In non-OSA applications a resistive, turbulent design is acceptable since noise or higher pressure is of no concern to the user. (2) The Agdanowski device also does not allow the nasal prong portion to align correctly with the user's nostril canal.

However, alignment is key in OSA applications because unaligned prongs are uncomfortable. For example, Winthrop, U.S. Pat. No. 5,682,881 describes an interface tubes with an adhesive-backed foam strip placed on the skin below the nose for securing the interface tubes system in place. While adhesive backed securement systems are common is various short-term therapy applications, their viability in long term or repeated use is questionable. The Winthrop device also has the airflow resistance and alignment problems previously noted.

Trimble, U.S. Pat. No. 4,782,832 describes a nasal interface with a hard manifold positioned under the nose from which two frustoconical corrugated members extend for insertion into and sealing against the nostrils. The manifold is suspended below the nose by a bracket extending down from the forehead between the eyes and down the bridge of the nose. A gas supply tube is attached to the bracket. This bracket and manifold arrangement is an improvement for users who want the tubing away from their mouth or ears, however this configuration is obtrusive and not conducive to vision especially if wearing glasses. Additionally, discomfort from the hard plastic brackets and manifolds are common. Similar designs are described in Bordewick, et al., U.S. Pat. No. 6,418,928, and Bordewick U.S. Pat. No. 6,431,172. This family of devices is known commercially as the ADAM (airway delivery and management) Circuit or Nasal Pillows.

Wood, U.S. Pat. No. 6,478,026 describes a PAP nasal interface tubes comprised of a conventional oxygen interface tubes tubing configuration (a horizontal base tube positioned under the nose from which two prongs extend upward at right angles for insertion into the nostrils). The prongs comprise oval cross sections and a concentric ring at their tips. Similar designs are described in Wood, U.S. Pat. No. 6,595,215, Wood, U.S. patent application Ser. No. 2002/0092527, Strickland U.S. Pat. No. 6,679,265, and Wood, U.S. patent application Ser. No. 2003/0116163.

Interface tubes prongs with oval cross sections have been in commercial use since at least 1987, for example in Trimble, U.S. Pat. No. 4,782,832, however, an oval cross section has no practical value for PAP usage. The prong material must be significantly more compliant than the nostril tissue for the requisite comfort, and hence the nostril structure will shape the prong to conform to the nostril regardless of the shape of the prong. Indeed, in pediatric and adult applications, a prong with a circular cross section is as comfortable and seals as well as does an oval cross section prong, assuming they are both fabricated using the correct material softness.

Additionally, some of the devices have the problems of requiring deep interface cannulation of the prongs into the nose for sealing and retention; deep interface cannulation is highly undesirable to many users and may cause mucosal irritation or errosion. Finally, this family of inventions still possesses the nostril-prong alignment problems, flow turbulence problems, obtrusiveness, ear and cheek discomfort, and discomfort while user is lying on their side.

MacRae, U.S. Pat. No. 6,644,305 describes a medicine inhaler that has a waist-shaped tip that seals with the nostril. De Voss, U.S. patent application Ser. No. 2002/0046756 describes an oxygen nasal interface tubes with left and right nostril prongs that pinch the nasal septum in order to retain the device in place. Pinching is accomplished by tilting the distal tips toward each other and the tilt and spacing can be adjusted in order to produce enough pinching force to achieve retention. This design is unacceptable in many PAP applications, because a pinch force of greater than about 2 lbs. compression is required for adequate pinching in adults, which cannot be tolerated for extended durations. A slight amount of repeated or long term pinching can be tolerated (<1 lbs.), however this is insufficient for retaining an interface tubes in place.

Light nostril septum pinching by PAP nasal interface tubes has been previously successfully employed in the art described in Trimble U.S. Pat. No. 4,782,832 and Wood U.S. Pat. No. 6,478,026, however in these cases other primary retention features are used to secure the apparatus in place and septum pinching is a secondary retention feature and likely less than 1 lbs. compression.

Curti, U.S. Pat. No. 6,439,234 describes a non-sealing oxygen nasal interface tubes with exhalation CO2 sampling. The base tube between the nasal prongs is divided to create two separate tubing paths, one for oxygen delivery (inhalation) and one for CO2 sampling (exhalation). This device has utility in anesthesia situations where CO2 monitoring is necessary and its teachings and embodiments are considerably different than that which is required for PAP applications.

In summary there are five significant requirements of a PAP nasal interface tubes interface that are not adequately addressed in patient interface devices especially for OSA applications: (1) low resistance flow dynamics; (2) a comfortable and effective nostril seal without requiring deep penetration into the nose; (3) a simultaneously comfortable, unobtrusive and non-irritating system to retain the device to the nose, face and head; (4) a system or device that is easy to attach and remove; and (5) the overall apparatus must be minimally obtrusive, comfortable and ergonomic, allowing a user to speak, see, wear glasses, drink, and talk on the phone while being worn before falling asleep, and allowing the user to comfortably lay on their side during sleep without shifting the device or dislodging the portion that seals to the nose. Most of the prior art is useful and applicable only for PAP applications in which the patient is unconscious or heavily sedated thus unaware of the noted deficiencies.

As will be described in the subsequent sections, the present invention(s) disclosed herein solves the various deficiencies that exist with the currently available PAP nasal interface tubes devices, especially with respect to the requirements of an OSA user.

SUMMARY OF THE INVENTION

Disclosed in this invention is a unique PAP nasal interface tubes ventilation interface comprising: (1) nasal prongs that are arcuately curved and non-angulated to minimize flow resistance, turbulence and noise; (2) freely moveable prong alignment and spacing to permit optimal alignment of the prongs with the nostril foramen to optimize comfort to the user; (3) a nostril sealing cushion engageable with the nostril rim to effect sealing without deep interface cannulation; (4) a strap securement system that provides (a) an upward compression force for the sealing cushions to stay engaged on the nostrils, and (b) that provides minimally obtrusive and maximally comfortable retention of the apparatus to the nose, face and head. Additional novel and unique features are also disclosed such as improved exhaust vent ports, mouth closure, concurrent supplemental oxygen delivery and aromatherapy.

In one aspect of the invention, a nasal ventilation interface including a pair of tubes configured to deliver a ventilation gas, the tubes attachable at a first end to a ventilation gas supply hose and engageable at a second end with a person's nostril; and a coupler configured to align the pair of tubes with the person's nostrils, wherein each tube has an absence of pneumatic interconnection with the other tube.

In another aspect of the invention, a kit comprising a pair of tubes configured to deliver a ventilation gas, the pair of tubes attachable at a first end to a ventilation gas supply hose and engageable at a second end with a person's nostril; a coupler configured to align the pair of tubes with the person's nostrils, wherein each tube has an absence of pneumatic interconnection with the other tube; and at least one pair of sealing cushions configured to be attachable to the second end of each ventilation interface tube and configured to impinge the nostril.

In a further aspect of the invention, an apparatus for supplying ventilation gas, the apparatus includes a connector configured to be attachable to a ventilation gas supply; a pair of tubes extending from the connector and configured to impinge a rim of a user's nostril such that a pressurized gas from the ventilation gas supply can be supplied to the person's respiratory system; and a coupler configured to align the pair of tubes with the person's nostrils, wherein each tube has an absence of pneumatic interconnection with the other tube.

In another aspect of the invention, a method of receiving a pressurized gas comprising positioning a ventilation interface device on a patient, the ventilation interface device comprising a pair of tubes configured to deliver a ventilation gas, the pair of tubes attachable at a first end to a ventilation gas supply hose and engageable at a second end with a person's nostril; a coupler configured to align the pair of tubes with the person's nostrils, wherein each tube has an absence of pneumatic interconnection with the other tube; and securing the ventilation interface with a first strap extending laterally over the ears from underneath the nose such that the first strap provides upward lift.

In one aspect of the invention, a nasal ventilation interface comprising a distal end configured to engage a user's nostrils; a proximal end configured to attach to a ventilation gas supply; and a mid-section between the proximal and distal ends, wherein the distal end and the mid-section comprises a pair of tubes having an arcuate non-angulated shape and having an absence of pneumatic interconnections between each of the tubes of the pair.

In a further aspect of the invention, a nasal ventilation interface comprising a pair of tubes configured to engage a user's nostrils at a distal end, wherein the distal end of the tubes comprise a substantially straight centerline axis, and further comprising a proximal end configured to attach to a ventilation gas supply hose; and a coupler configured to connect the pair of tubes having a movable joint between the pair of tubes, wherein the movable joint comprises a swivel to permit rotational movement of the tubes in at least one plane, wherein the movement is used to substantially align the axial centerline of each tube with a nostril foramen.

In another aspect of the invention, a nasal ventilation interface for the purpose of supplying ventilation gas to a person's airway, the interface comprising a generally tubular construction with a distal end configured with a first and a second tube for engagement with a person's nostrils, a proximal end configured for attachment to a ventilation gas supply hose, and a coupler connecting the first and second distal ends of the tubes, and further comprising a lifting means applied substantially directly under the nose to the distal end of the first and second tubes, wherein the lift creates and maintains an engagement force between the tubes' distal tip and the nostrils, and further wherein the lifting means comprises a first strap attached to the head over and behind the ears.

In a further aspect of the invention, a nasal ventilation interface apparatus for the purpose of supplying ventilation gas to a person's airway, the apparatus comprising a generally tubular construction with a distal end comprising a first and second tube configured to engage a person's nostrils, a proximal end configured to attach to a ventilation gas supply hose, wherein the distal end comprises a facial pad positioned between the tubes and the skin between the user's nose and upper lip, wherein the facial pad cushions the user's skin and tilts the distal end tubes in an angle in the sagittal plane wherein the angle aligns the distal end tubes with the rim of the user's nostril.

In another aspect of the invention, a nasal ventilation interface apparatus for the purpose of supplying ventilation gas to a person's airway comprising a generally tubular construction with a distal end comprising a first and a second tube configured to engage a person's nostrils, a proximal end configured to attach to a ventilation gas supply hose, further comprising a band member substantially circumventing the head from the chin to the top of the head, wherein the band applies upward compression on the chin so as to bias the mouth in a close state, and wherein the band comprises means to attach the apparatus to the band member.

The above aspects of this invention are more fully explained in reference to the drawings and general disclosure herein.

BRIEF DESCRIPTION OF THE DRAWINGS

The invention will now be described in greater detail with reference to the preferred embodiments illustrated in the accompanying drawings, in which like elements bear like reference numerals, and wherein.

DESCRIPTION OF THE INVENTION

Nasal Interface

Figure 1:
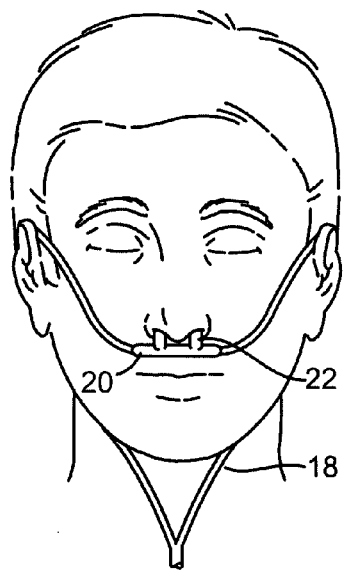
FIG. 1 shows a front view of a conventional nasal interface cannula for positive pressure ventilation.
Figure 2:
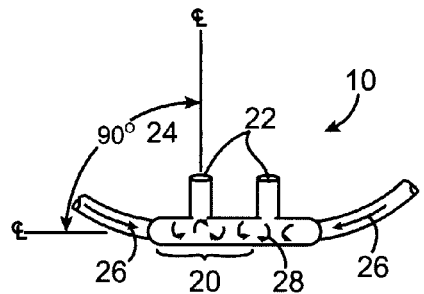
FIG. 2 shows a perspective of the conventional nasal interface cannula of FIG. 1.

FIGS. 1 and 2 show a perspective view of a conventional positive airway pressure (PAP) nasal interface 10. The nasal interface 10 comprises a base manifold 20 positioned below the nose from which two nasal prongs 22 extend at right angles 24 upward into the nose. The base manifold 20 typically receives airflow 26 from both directions causing turbulent mixing and high resistance 28. The sudden directional change of the airflow up into the two nasal prongs 22 adds to the high resistance and turbulent flow 28 within the manifold 20. The tubes wrap around the ears and extend to the below the chin 18.

Figure 3A:
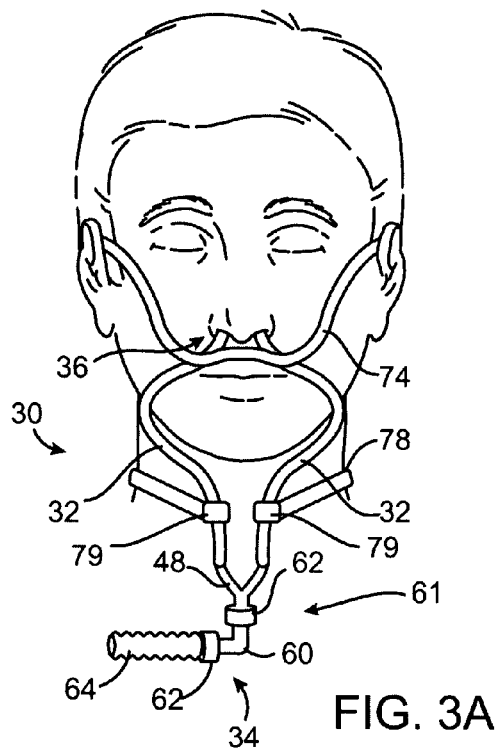
FIG. 3A shows a front view of a nasal interface according to one embodiment of the present invention.

FIG. 3A shows a perspective view of a nasal interface device 30 according to one embodiment of the present invention. The device 30 comprises a pair of ventilation interface tubes 32 which are configured to deliver a ventilation gas to a user. The tubes 32 are attachable at a first end 34 to a ventilation gas supply hose 64 and engageable with a person's nostrils at a second end 36. Each tube 32 has an absence of pneumatic interconnection with the other tube 32 providing laminar flow to the nostrils.

As shown in FIG. 3A, the ventilation gas supply hose 64 is attachable to the pair of tubes 32 with a bifurcation device 61. The bifurcation device 61 is preferably a Y-connector 48. However, it can be appreciated that other shapes and configurations can be used to bifurcate the gas supply hose into at least two tubes 32. The bifurcation device 61 also preferably comprises at least one swivel 62. As shown in FIG. 3A, the bifurcation device 61 can further include at least two swivels 62, a hose coupler 60 and the Y-connector 48.

The pair of tubes 32 preferably impinge the rim of the nostrils at the second end 36. As shown in FIG. 3A, the device 30 can be secured to the user by a combination of a first strap 74 in the form of a headband and a second strap 78 in the form of a neckband. The first strap 74 preferably attaches to the pair of tubes 32 just below the user's nostril by a suitable means. The first strap 74 preferably extends from just below the user's nostril and over the user's ears connecting behind the back of the user's head. It can be appreciated that the interface device 30 can be secured to the user's face by any suitable means.

In an alternative embodiment, a second strap 78 can be used to attach the interface device 30 to the neck area of the user. As shown, the second strap 78 is attachable to each of the tubes 32 at a location between the bifurcation device 61 and the second end of the device 36. The second strap 78 can preferably be attachable to the interface tubes 32 by any suitable means including a snap lock, Velcro, fabric loop, clip, and other suitable attachment devices.

Figure 3B:
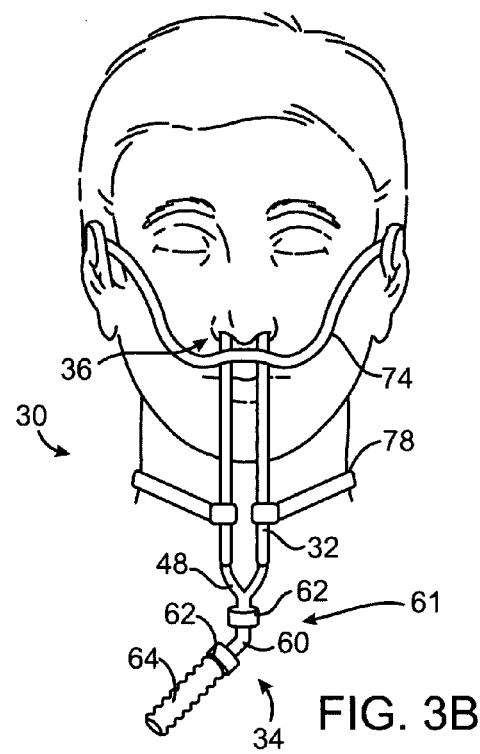
FIG. 3B shows a front view of the nasal interface of FIG. 3A according to another embodiment.

FIG. 3B shows a perspective view of another embodiment of the nasal interface device as shown in FIG. 3A. As shown in FIG. 3B, the ventilation gas supply hose 64 is attachable to the pair of tubes 32. The pair of tubes 32 extend directly from the bifurcation device 61 to the nostrils without an arcuate shape as shown in FIG. 3A.

The hose coupler 60 is configured to direct the gas supply hose 64 away from the body. The hose coupler 60 is preferably an angled member having an angle of approximately 90 degrees to approximately 180 degrees. As shown in FIG. 3A, the hose coupler 60 is a 90 degree angle. Meanwhile, the hose coupler 60 as shown in FIG. 3B has an angle of approximately 120 degrees.

Figure 4:
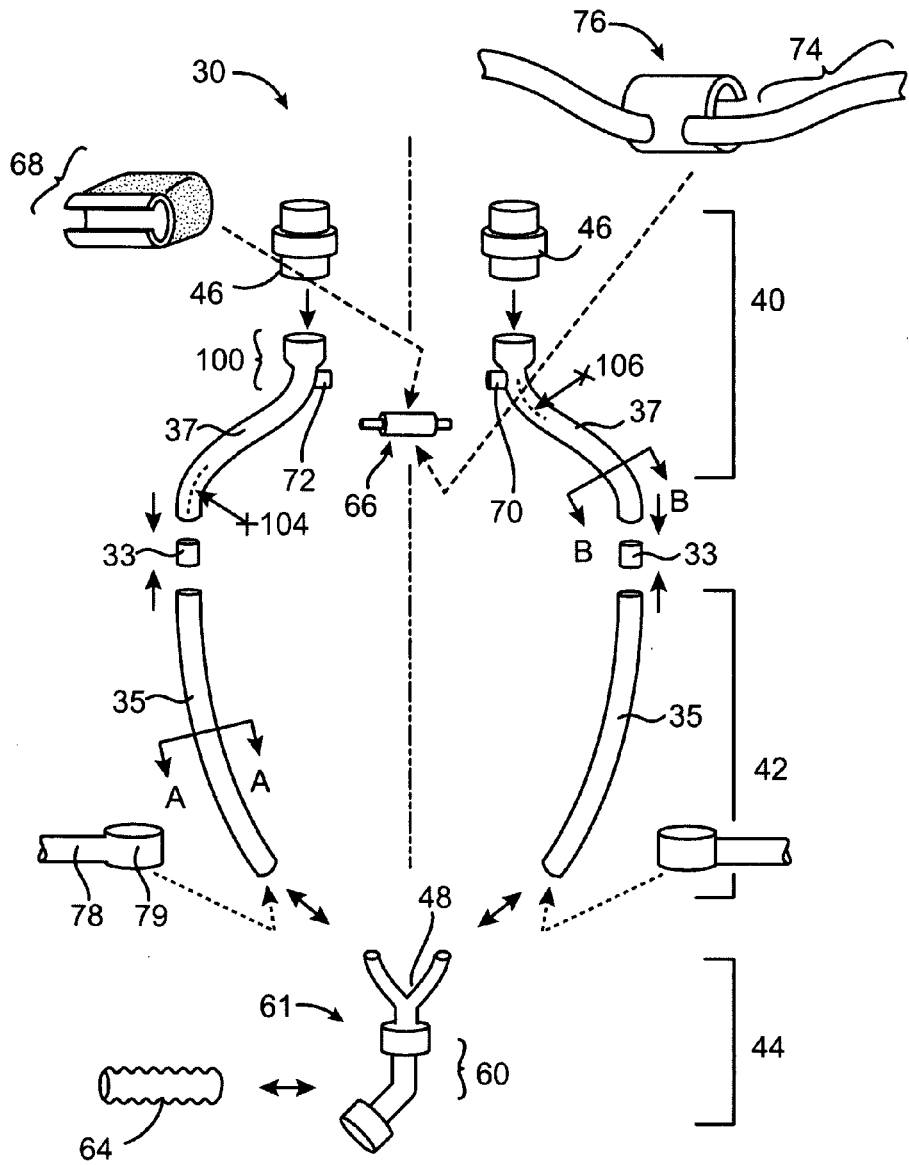
FIG. 4 shows an exploded perspective view of the nasal interface of FIG. 3A.

FIG. 4 shows an exploded perspective view of a nasal interface device 30 according to another embodiment of the present invention. As shown in FIG. 4, the device 30 is generally comprised of a tubular construction, and can be comprised of three basic sections; a distal section 40, a midsection 42 and a proximal section 44.

The distal section 40 comprises a pair of sealing cushions 46, a pair of delivery tubes 37, and a connector 33. As shown in FIG. 4, the pair of tubes 32 as shown in FIG. 3 can be separated into a pair of supply tubes 35 positioned within the midsection 42 of the device 10 and a pair of delivery tubes 37 positioned within the distal section 40 of the device 30. Alternatively, the pair of tubes 32 can be, as shown in FIGS. 3A and 3B, one continuous tube extending from the gas supply hose 64 to the distal end 36.

The pair of delivery tubes 37 can be configured to engage the rim of the user's nostril or nares or alternatively a pair of sealing cushions 46 can be attached to the distal end 36 of the delivery tubes 37. As shown, the supply tube 35 is preferably attachable to the ventilation gas supply hose 64 via a Y-connector 48 at one end and to the pair of delivery tubes 37 at the other end with the connector 33.

In a preferred embodiment of the present invention, the pair of interface tubes 32 comprising the pair of delivery tubes 37 and the pair of supply tubes 35 are unconnected pneumatically to each other. However, the pair of tubes 32 can be mechanically connected via a mechanical coupler 66 with a left and right coupler connector 70 and 72. In addition, the interface tubes 32 are preferably void of abrupt angles from the proximal end to their distal end of each of the tubes 32. As shown in FIG. 4, the distal end of each of the interface tubes 32 preferably comprise a terminal section 100, which is axially substantially straight (but not necessarily absolutely straight) for engagement with or for minor insertion into the nostrils.

At the inferior base of these distal straight terminal sections 100 the interface tubes 32 assume the most gradual curvatures 104 and 106 as possible while still fitting within the anatomy. The interface tubes 32 may curve and extend away from the nostrils in several possible configurations. In the preferred configuration the interface tubes 32 curve first laterally 106 then inferiorly 104 toward the ventral aspect of the neck, typically lateral to the corners of the mouth. It can be appreciated that the tubes 32 are curve posteriorly. This curved non-angulated configuration minimizes flow resistance thus minimizing turbulence, leakage, noise and the required pressure level. Airflow resistance of this invention is approximately 25% less than that of conventional PAP nasal cannulae (which is more resistive for the reasons described previously).

Figures 16A, 16B, 16C, 16D, 16E:
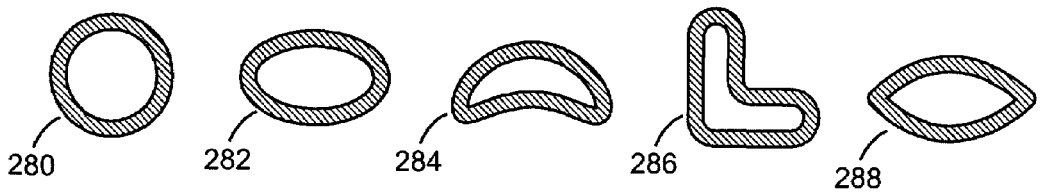
FIGS. 16A-16E show a cross-sectional view of the various sealing cushions along line E-E of FIG. 14D.

In a further embodiment of the present invention as shown in FIG. 4, the distal section 40 of the device 30 is preferably equipped with a pair of sealing cushions 46 that impinge the nostrils. The sealing cushions 46 are attachable to a distal end of each of the pair of tubes 32. The sealing cushions 46 position the interface tubes 32 against the nostril rim to provide a leak free connection between the sealing cushion 46 and the interface tubes 32, and to prevent dislodgment of the sealing cushions during use. As shown in FIGS. 14, 15 and 16, the sealing cushions 46 can be configured in any suitable shape and cross-sectional design to insure proper sealing and comfort. The shape of the sealing cushions 46 including the cross-sectional design also provides comfort to the user.

The distal section 40 is preferably secured to the user by the first strap 74 or headband. As shown in FIGS. 3A and 3B, the first strap 74 preferably attaches to the pair of tubes 32 just below the user's nostril by a suitable means. As shown in FIG. 4, the first strap 74 is attachable to the interface tubes 32 via a connector 76. The first strap 74 preferably extends from just below the user's nostril and over the user's ears connecting behind the back of the user's head. It can be appreciated that the interface device 30 can be secured to the user's face by any suitable strap, band or retention device.

The connector 76 is preferably attached to the coupler 66 to secure the device 30 to the nose, face and head. An additional strap or second strap 78 can be provided for attachment of the interface tubing 32 in the mid-section 42 to the neck to help secure the device to the body. It can be appreciated that in an alternative embodiment, the mid-section 42 disconnects from at least the distal section 40, allowing separation of the interface tubing 32, as needed.

As shown in FIG. 4, the distal section 40 comprises a pair of sealing cushions 46, a mechanical coupler 66 and the second or distal ends of the pair of tubes 32. In a preferred embodiment of the present invention, the pair of interface tubes 32 is joined under the nose with the mechanical coupler 66. The coupler 66 is configured to adjust the spacing 120 (FIG. 6) of the pair of distal tips to match the user's anatomy.

It can be appreciated that in a preferred embodiment, immediately proximal to the soft sealing cushions 46, the pair of tubes 32 is attached with a coupler 66. A tilt pad 68 can be attached to the coupler 66 or to one of the neighboring interface tubes 32 for the purpose of padding the skin to absorb strapping forces and aligning the angle of the distal tips of the device with the user's nostrils.

The mid-section 42 comprises symmetrical tubes of either the interface tubes 32 or as shown in FIG. 4 the supply tubes 37. If a second strap 78 is provided the supply tubes 37 are attached to the second strap 78 via a loop connector 79. It can be appreciated that the second strap 78 can be attached by any suitable connector to the interface tubes 32.

As shown in FIG. 4, at the proximal end 44, the pair of tubes 32 joins at a bifurcation site 48. The bifurcation site 48 is preferably substantially proximal to the distal end 36. However, it can be appreciated that the bifurcation site 48 does not have to be substantially proximal to the distal end 36 and can be positioned more distal to the distal end 36 of the device 30. Between the distal tip and the bifurcation site 48, the device 30 is comprised of generally symmetric construction. Preferably, the pair of tubes 32 is not in communication pneumatically other than at the site of bifurcation 48.

The nasal interface device 30 is preferably made of biocompatible, hypoallergenic materials or other suitable materials. In addition, the device 30 can be treated with antimicrobial, hydrophilic or lubricious surface treatments to prevent unfavorable tissue response.

The interface tubes 32 including the supply tubes 35 and delivery tubes 37 are preferably made of material such as polyvinyl chloride (PVC), plastisol, silicone, urethane, urethane-PVC blends, synthetic thermosets or combinations thereof. It can be appreciated that the device 30 can be made from any suitable material.

The interface tubes 32 preferably have an inner diameter of about 8 mm to about 16 mm for adults, about 5 mm to about 8 mm for pediatrics, and about 1 to about 5 mm for neonates. In addition, the interface tubes 32 preferably have a durometer of about 30 A Shore to about 80 A Shore for the tubes 32 and a durometer of about 10 A to about 70 A for the distal end 36 and/or sealing cushions 46.

Figure 5A:
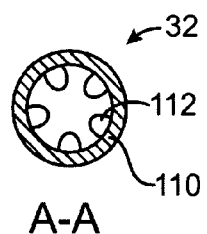
FIG. 5A shows a cross-sectional view of the nasal interface of FIG. 4 along the line A-A.
Figure 5B:
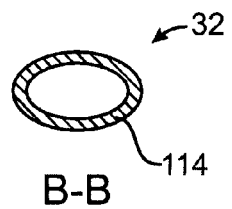
FIG. 5B shows a cross-sectional view of the nasal interface of FIG. 4 along the line B-B.

FIGS. 5A and 5B show a preferred embodiment of a cross-sectional view of the pair of interface tubes 32 in the distal section 40 and the mid-section 42 of the device 30, respectively. As shown in FIG. 5A, the cross-sectional shape of the tubing 32 at the mid-section 42 is round 110. However, it can be appreciated that the cross-sectional shape of the distal section 40 or mid-section 42 of the interface tube 32 can include longitudinal or radial ribs 112 to prevent kinking. As shown in FIG. 5B, the interface tubes 32 in the distal section 40 preferably have a flatter profile 114 so as to be less obtrusive to the user, or can comprise radial corrugations in strategic locations to provide flexure of the device 30 to mate with the individual's anatomy. Alternatively, the device 30 can comprise shape-memory or malleable shape-able members within its construction to allow the pair of interface tubes 32 to be curved optimally to fit the individual's anatomy.

Preferably, the distal section 40 of the nasal interface device 30 is injection molded to its final shape. However, the distal section 40 can be extruded or injection molded straight then bend-formed to its final shape, or dip formed, or can be shapeable by the user. The proximal section of the device 30 is preferably extruded and optionally bend-formed into the desired curved shape that matches a stereotypical chin and neck anatomy. It can be appreciated that the combination of injection molding, extruding or injection molded straight and then bend-formed into the desired shape can be used to manufacture the interface device 30.

Figure 6:
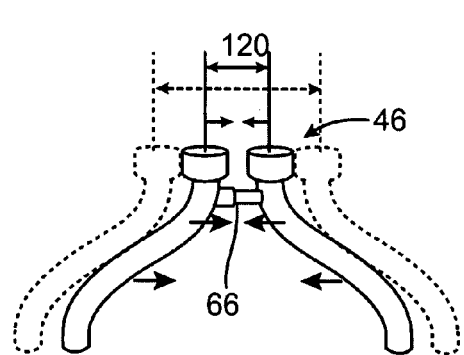
FIG. 6 shows a perspective view of a coupler according to one embodiment of the present invention.

FIG. 6 shows a perspective view of a portion of the distal section 40 of the device 30. As shown in FIG. 6, the distal section 40 comprises a pair of sealing cushions 46 and the second or distal ends of the pair of interface tubes 32. In a preferred embodiment of the present invention, the pair of interface tubes 32 is joined under the nose with a mechanical coupler 66. The coupler 66 is configured to adjust the spacing 120 of the pair of distal tips or sealing cushions 46 to match the user's anatomy.

The coupler 66 is preferably a plastic tubular member of approximately 60-80 Shore A durometer. The coupler 66 is preferably extruded and then formed to create the joints, or alternatively injection molded.

Figure 7:
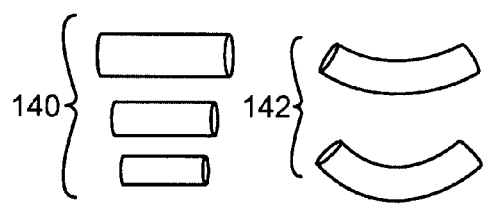
FIG. 7 shows a perspective view of various couplers as shown in FIG. 6.

As shown in FIG. 7, the coupler 66 can be removably attached to the interface tubes 32 in which case there may be a variety of sizes 140 or shapes 142. The variety of sizes 140 or shapes 142 can be select based on the user's anatomy.

Figure 8A:
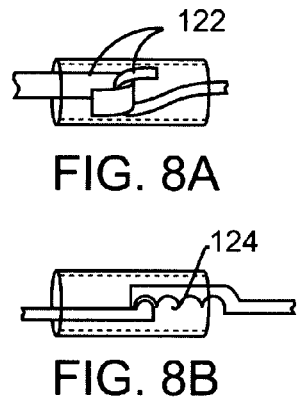
FIGS. 8A-8G show perspective views of the coupler according to FIG. 6 having various method of adjusting the length of the coupler according to various aspects of the present invention.
Figure 8B:
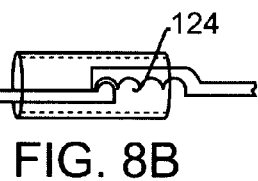
Figure 8C:
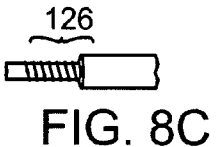
Figure 8D:
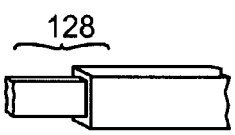
Figure 8E:
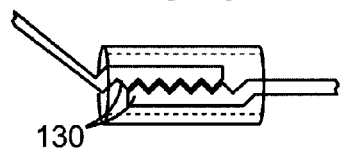
Figure 8F:
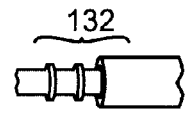
Figure 8G:
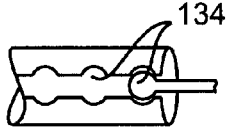

Alternatively, as shown in FIGS. 8A-8G, the coupler 66 can be permanently affixed to the pair of interface tubes 32, in which case the coupler 66 preferably comprises an adjustment feature to adjust or change the length of the coupler 66. The length of the coupler 66 can be adjusted by the use of opposing hooks 122 (FIG. 8A), a ratchet 124 (FIG. 8B), a threaded system 126 (FIG. 8C), a tongue and flat groove 128 (FIG. 8D), an opposing saw tooth 130 (FIG. 8E), opposing connectable tubes 132 (FIG. 8F), or a ball and socket 134 (FIG. 8G). It can be appreciated that the length of the coupler 66 can be adjusted using any suitable device.

Figure 9:
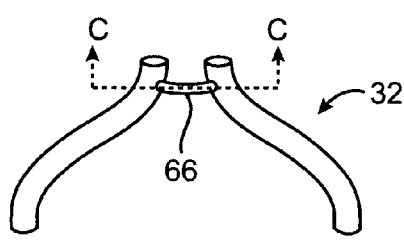
FIG. 9 shows a perspective view of an alternative embodiment of the coupler, wherein the coupler has a lumen that communicates pneumatically with the tubes of the interface device.
Figure 10:
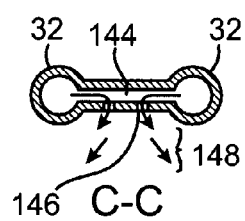
FIG. 10 shows a cross-sectional view of the coupler of FIG. 9 along the line C-C.

In an alternative embodiment as shown in FIGS. 9 and 10, the coupler 66 can further comprise a lumen 144 that communicates pneumatically with the pair of interface tubes 32. The lumen 144 is preferably substantially smaller and more resistive to airflow than the interface tubes' main lumen so as to limit airflow into the coupler to avoid generating backpressure into the interface tubes 32 lumens. However, it can be appreciated that the lumen 144 can be substantially smaller, smaller, equal or substantially larger than the interface tubes 32 main lumen. In addition, it can be appreciated that the coupler lumen 144 can include exhaust vent ports 146 allowing venting of an exhaled gas 148 and $CO_2$ out of the coupler 66.

Figure 11A:
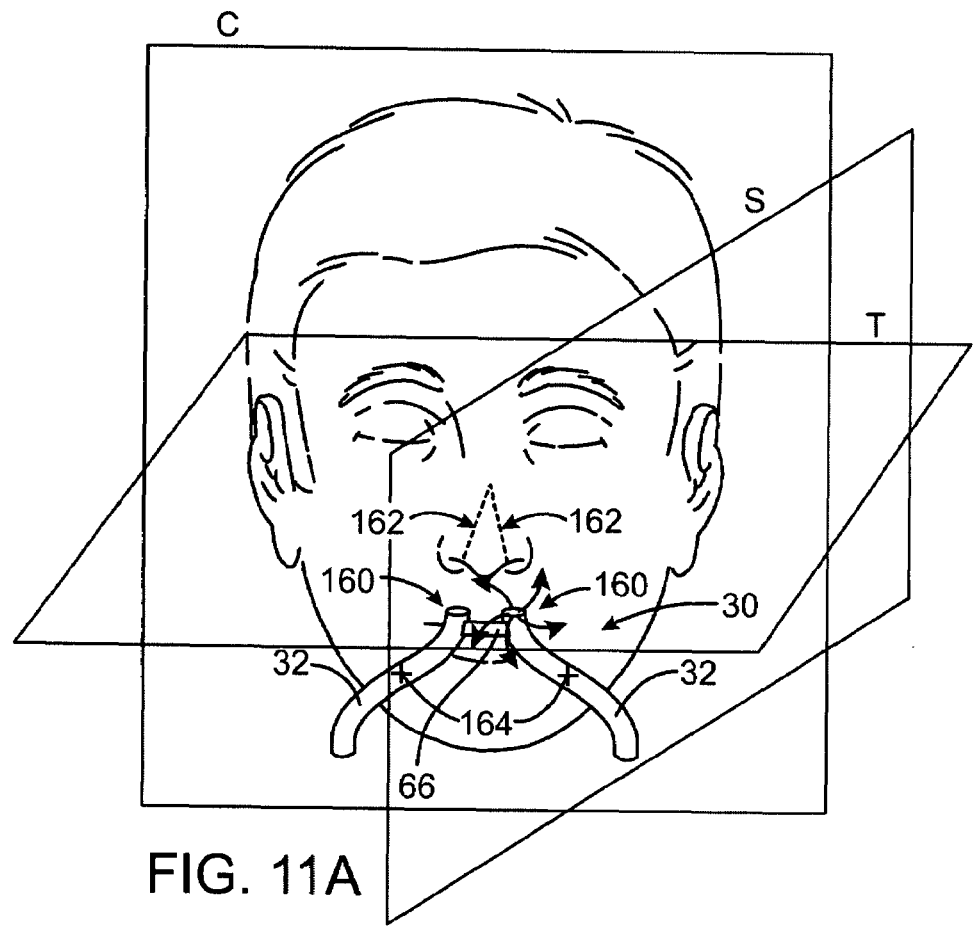
FIG. 11A shows a plan view of various angle of adjustment of the interface tubes configured to align the tubes with the nostrils of the nose.
Figure 11B:
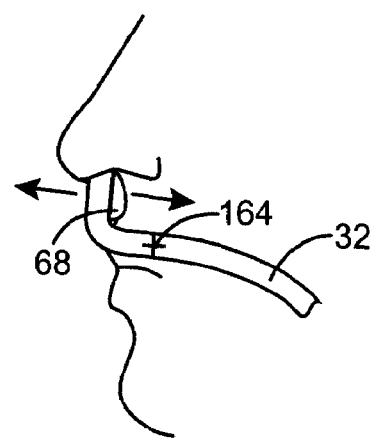
FIG. 11B shows a side view of the various angles of adjustment of the interface tubes of FIG. 11A.

FIGS. 11A and 11B show a front and side view of the interface device 30 based on a user's facial anatomy. As shown in FIGS. 11A and 11B, the second or distal ends 36 of the interface tubes 32 can swivel in multiple planes from a roughly fixed origin 164 in order to align the centerline axis of the distal tips 160 with the centerline axis of the nostril canals 162. Because there is a vast variety of nose shapes, sizes, and angles, and because proper alignment is essential for comfort, angle adjustability in multiple planes is essential especially in OSA applications. In order to achieve a proper alignment, the interface tubes 32 can swivel in the sagittal plane S, the coronal plane C and the transverse plane T.

As shown in FIGS. 11A and 11B, the sagittal plane S generally relates to the suture between the parietal bones of the skull or situated in or being in the medial plane of the body or any plane parallel thereto. The coronal plane C relates to lying in the direction of the coronal suture or relating to the frontal plane that passes through the long axis of the body. Meanwhile, the transverse plane T is at right angles to the anterior-posterior axis of the body.

Figure 12:
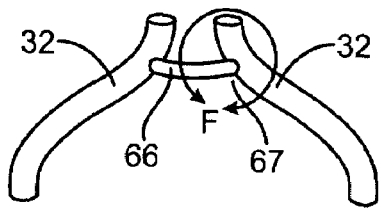
FIG. 12 shows a perspective view of the connection between the coupler and interface tubes.
Figure 13A:
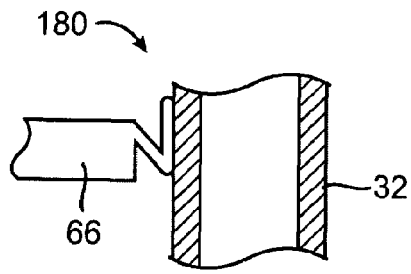
FIGS. 13A-13H show cross-sectional views of various connections between the coupler and interface tubes of FIG. 12.
Figure 13E:
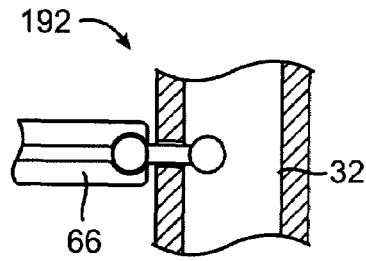
Figure 13B:
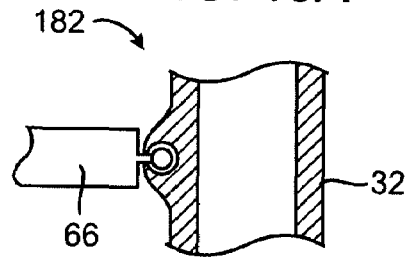
Figure 13F:
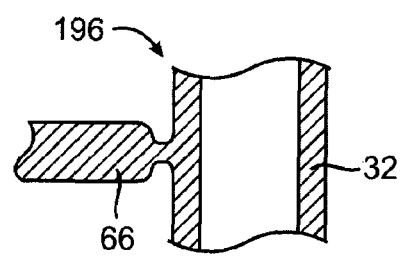
Figure 13C:
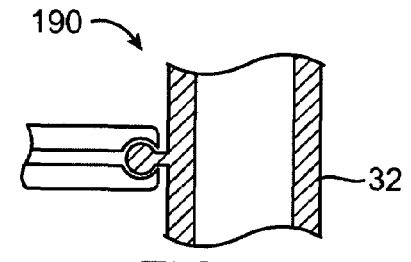
Figure 13G:
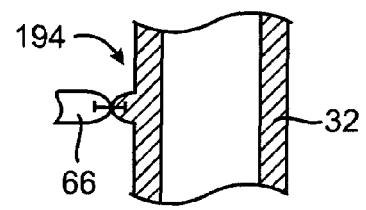
Figure 13D:
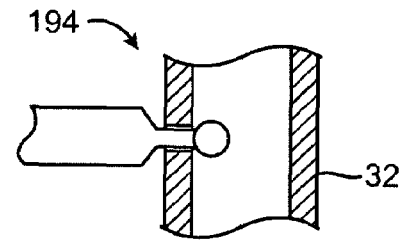
Figure 13H:
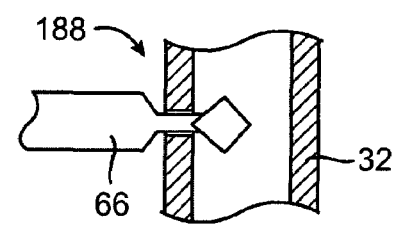

FIG. 12 shows a perspective view of another aspect of the present invention further comprising a movable joint 67 between the coupler 66 and the distal end of the interface tubes 32. The movable joint 67 allows free movement of the distal end of the interface tubes 32 in order to permit alignment of the sealing cushions 46 and the rim or entrance of the nostril canals.

As shown in FIGS. 13A-13H, the movable joint 67 can be a hinge joint 180 (FIG. 13A), a ball and socket swivel joint 182 with the ball attached to the interface tubes 32 (FIG. 13B), a ball and socket swivel joint 190 with the ball attached to the coupler 66 (FIG. 13C), a gliding joint 194 with a coupler ball inserted into the interface tubes lumen (FIG. 13D), a combination of a ball and socket swivel joint with a glide joint 192 (FIG. 13E), a pivot joint 196 optionally with an inserted tie bar (FIG. 13F), a gliding joint with a catch feature inserted into the interface tubes lumen 188 (FIG. 13H), a flex joint 194 (FIG. 13G), or any combinations thereof. It can be appreciated that the movable joint 67 can be any suitable joint and that the embodiments as provided are examples only.

The joints between the interface tubes 32 and the coupler 66 can be insert molded, bonded or press fit into the respective components.

Figure 14C:
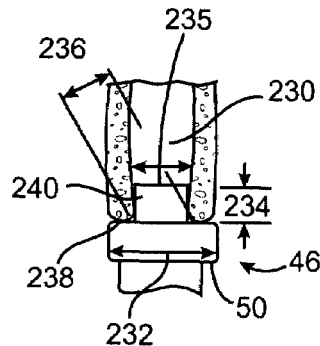
FIG. 14C shows a cross-sectional view of the sealing cushion of FIG. 14A along the line D-D.
Figures 14B, 14D:
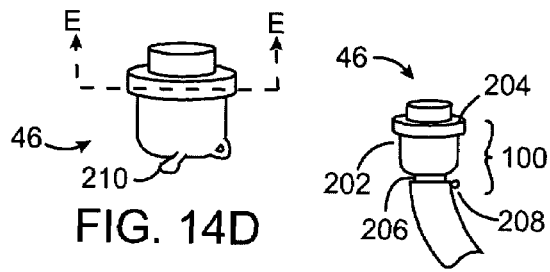
FIG. 14B shows a perspective view of the sealing cushion of FIG. 14A.
FIG. 14D shows a perspective view of a sealing cushion.
Figure 14A:
FIG. 14A shows a front view of a sealing cushion configured to seal against a rim of the nostril, including a stepped cushion profile for engagement and sealing to the nostril rim.

FIG. 14A shows a front view of the distal tips 100 of the interface tubes 32, which are equipped with sealing cushions 46. As shown in FIG. 14A, the sealing cushions 46 and seal the nostril. In addition, the sealing cushions 46 prevent the interface tubes 32 from penetrating deep into the nostril. The sealing cushions 46 are preferably removably attachable from the interface tubes 100.

As shown in FIG. 14A, the sealing cushions 46 and the interface tubes 32 are designed to assure (1) proper positioning of the sealing cushion 46 against the nostril rim, (2) a leak free connection between the sealing cushion 46 and the interface tubes 32, and (3) prevent inadvertent dislodgement of the sealing cushion 46 during use.

FIG. 14B shows a perspective view of a sealing cushion 46 and distal end 100 of the interface tubes 32, comprising a step 202, a ridge 204, a groove 206, and a button or hook 208. The sealing cushion 46 can include a leash 210 (FIG. 14D) for grasping so that the sealing cushion 46 is easily installed and removed.

Figure 14E:
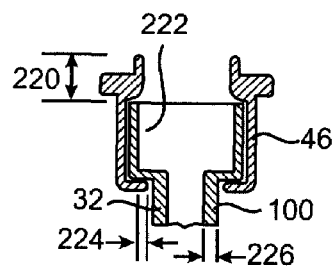
FIG. 14E shows a cross-sectional view of the sealing cushion.
Figure 15A:
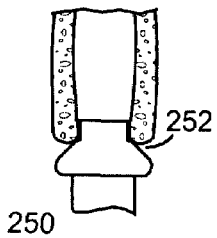
FIGS. 15A-15G show cross-sectional views of various sealing cushions according to a further embodiment of the present invention.
Figure 15B:
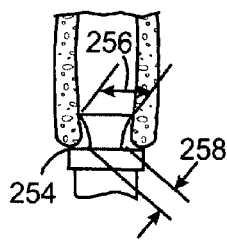
Figure 15C:
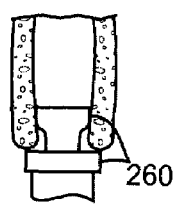
Figure 15D:
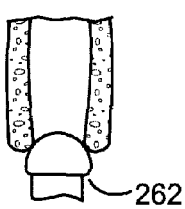
Figure 15E:
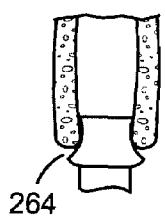
Figure 15F:
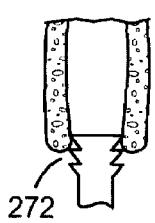
Figure 15G:
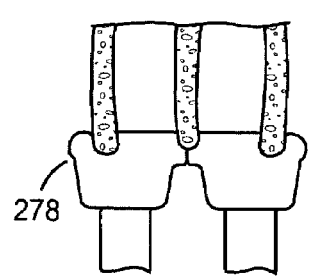

As shown in FIG. 14E, the sealing cushion 46 preferably extends 220 beyond the terminal section 100 of the interface tubes 32, such that the sealing cushion 46 enters the nostril rather than the terminal section 100 of the interface tube 32. It can be appreciated that the sealing cushions 46 can have any suitable cross sectional shape that provides a seal against the nostril of the noses. Thus, any variety of cross sectional shapes can be implemented and that the cross sectional shapes shown are only a few of the cross sectional shapes.

The sealing cushions 46 are preferably comprised of a soft thermoset or thermoplastic material of 45-60 Shore OO durometer. In addition, the sealing cushions 46 are preferably translucent or tinted to make it aesthetically pleasing or color coded, wherein each color is associated with a size and/or cross-sectional shape. The seal cushions 46 can be formed by extruding then shape forming, or by dip-molding or injection molding.

As shown in FIG. 14E, the terminal section 100 of the interface tubes 32 comprise an interface tube tip 222 position on the distal end of the interface tubes 32. The interface tube tip 222 is preferably of thinner wall thickness 224 than the thickness 226 of the balance of the interface tubes 32 to decrease the rigidity of the terminal section 100 in the event the tip is felt by the nostril.

FIG. 14C shows a stepped profile of a sealing cushion 46 with a first diameter 230 at the distal tip 235 and a second diameter 232 larger than the first diameter 230 at distance 234 from the distal tip 235, thus creating a stepped section 50. The larger diameter 232 is sized to be larger than a diameter of a nostril opening 236 and the smaller tip diameter 230 is designed to be approximately equal to or slightly less than the inner diameter of the nostril opening 236. Thus, the configuration seals on the outside rim 238 of the nostril and optionally seals along a depth on the inside surface 240 of the nostril. As shown, the engagement depth 234 is kept relatively shallow, preferably at a depth equal to about 5% to about 70% of the nostril diameter, and more preferably at a depth equal to about 20% to about 30% of the nostril diameter. However, it can be appreciated that the penetration can be greater or less than the diameters set forth above.

In addition, as shown in FIGS. 15A-15G, shape of the sealing cushion 46 is not limited to the configuration as shown in FIGS. 14A-14E. For example, the sealing cushions 46 can comprises a convex profile that curves inward 250 whereupon the nostril rim engages 252 on the curved inward surface (FIG. 15A), or a flared shaped sealing cushion 254 which at the distal tip flares to a larger diameter 256 than the base of the flare 258 such that the flared diameter seals on the inside diameter of the nostril at a distance in from the nostril rim (FIG. 15B), a double seal 260 (FIG. 15C), a mushroom profile 262 (FIG. 15D), a waist profile 264 (FIG. 15E), a reverse barb profile 272 (FIG. 15F), or a profile sealing around the outside of the nose 278 (15G).

Alternatively, the cross sectional profiles of the sealing cushions 46 can vary to match the anatomy depending on individuality variances. For example, the cross sectional profile of the sealing cushion can be circular 280 (FIG. 16A), an oval 282 (FIG. 16B), an arcuate 284 (FIG. 16C), an L-shaped 286 (FIG. 16D), an elliptical 288 cross sectional shape (FIG. 16E), or alternatively the cross sectional shape throughout the length of the cushion may vary. It can be appreciated that selection of different sizes and shapes can be available to optimize fit and comfort, as well as adjustability of the design, and the cushions may be shape-able by the user to match the desired shape.

Figure 17:
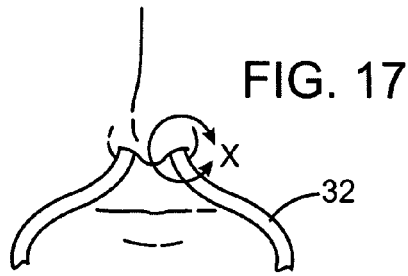
FIG. 17 shows a front view of another aspect of the sealing cushion.
Figure 18A:
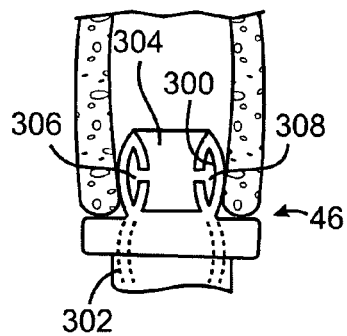
FIGS. 18A-C show a cross-sectional view of another aspect of the sealing cushion, wherein the sealing cushions are inflatable, application of a vacuum, and where the sealing cushion is part of the interface tubes, respectively.
Figure 18B:
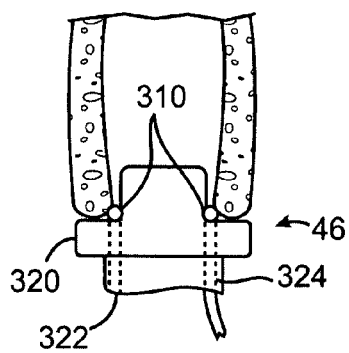
Figure 18C:
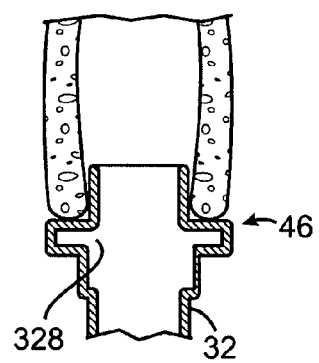

FIG. 17 shows a front view of another aspect of the sealing cushion 46, wherein the sealing cushions are inflatable (FIG. 18A), an application of a vacuum to the sealing cushion 46 is use (FIG. 18B), and where the sealing cushion 46 is part of the interface tubes 32 (FIG. 18C).

FIG. 18A shows a cross-sectional view of the sealing cushion 46, as shown in FIG. 17 in the area of nostril (X) that partially dilates or inflates 300 to seal against the nostril wall. Inflation can be performed by an inflation channel 302 communicating with the cushion, or by pressurization from the inside of the interface tube lumen 304 into the cushion space 306.

FIG. 18B shows a cross-sectional view of an alternative embodiment wherein the seal between the interface tube tip (or cushion) 320 and nostril wall is enhanced by application of a vacuum to the space between the interface tube and the nostril wall, either on the inside of the nostril or at the outside rim of the nostril 310 where continuous suction will not irritate the skin. Vacuum is delivered to the site through channels 322 in the interface tubing or through a separate vacuum tube 324. When applied, the vacuum sucks the nostril wall tissue into contact with the sealing cushion to create the seal.

FIG. 18C shows a cross-sectional view of a further embodiment in which the sealing cushion 46 is permanently connected to the nasal interface tubing 32, which may be more economically viable in single-use disposable applications such as emergency use. This one-piece design can be constructed by two pieces bonded or welded together or by a unitary design where the interface tubing material is thinned and reshaped 328 at the very tip to create the necessary softness and sealing shape.

Figure 18D:
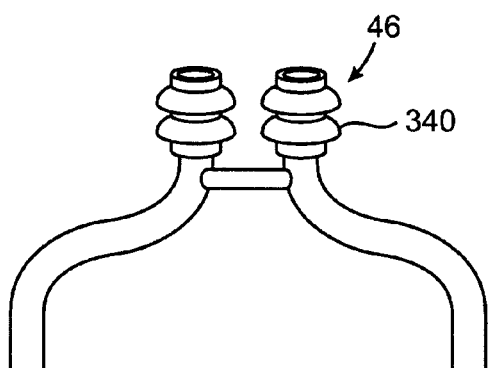
FIG. 18D shows a perspective view of a further aspect of the sealing cushions, wherein the sealing cushions are comprises of at least one ring.

FIG. 18D shows a perspective view of another embodiment of the sealing cushions 46, which are configured to fit within the nostril. As shown in FIG. 18D, the sealing cushion 46 comprises at least one disk 340, which is configured to fit within the nostril. The at least one disk 340 retains the sealing cushion 46 and tube 32 within the nostril by applying a minimum amount of pressure on the inside of the nostril. In order to spread out or distribute the force against the inside of the nostril, the sealing cushions 46 preferably comprises a plurality of disks 340. As shown in FIG. 18D, the sealing cushions 46 comprises two disks 340 having a downward shape or mushroom appearance.

Figure 18E:
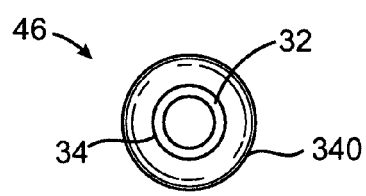
FIG. 18E shows a top view of a sealing cushion of FIG. 18D.

FIG. 18E shows a top view of the sealing cushion 46 of FIG. 18D. As shown, the sealing cushion 46 comprises at least one disk 340 extending around the lumen 34 of the sealing cushion 46.

Figure 19A:
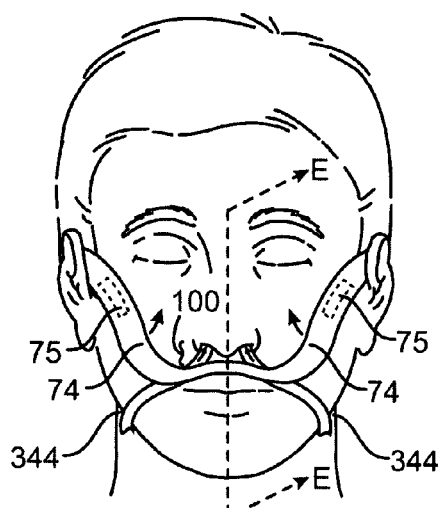
FIGS. 19A and 19B show a front and side view of a head strap configured to lift and compress the sealing cushions against the nose and secures the position of the interface tubes lateral to the nose.
Figure 19B:
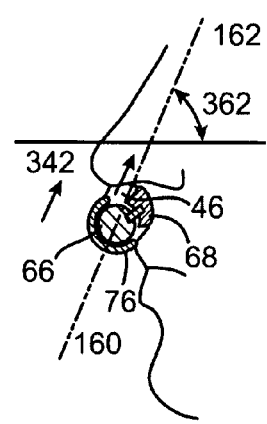

FIGS. 19A and 19B show a front view and a side view, respectively of a first strap 74, which connects to the coupler 66 at a rotational orientation at about 360 degrees opposite the nostril opening. The first strap 74 extends bilaterally, preferably over the ears, and is joined behind the head. The attachment orientation and overall configuration thus produces an upward lift 342 on the distal tips 235 of the sealing cushions 46 against the nostrils, thus compressing and retaining the sealing cushions 46 against the nostrils to facilitate and maintain a seal. The first strap 74 presses the interface tubes 32, lateral to the nose, against the skin 344 to help prevent inadvertent shifting of the interface tube 32 and the sealing distal tips.

The first strap 74 aides in retention of the device 30 to the user's face. Preferably at least a portion of the first strap 74 comprises an elastomeric material, such as a translucent highly elastic thermoset or thermoplastic material to enhance comfort and to reduce intrusiveness. Meanwhile, the balance of the first strap 74 is comprised of a fabric, such as a woven rubber-nylon blend. Alternatively, it can be appreciated in a further embodiment, the first strap 74 can further be comprised of a material, which provides padding on the skin side of the first strap 74, especially at the ear area or under the nose to further improve comfort. The attachment 76 to the coupler 66 can be a half-pipe that snaps onto a tubular-shaped coupler, or a snap, or a spring type catch, a loop or other easy attachment means, or the first strap 74 and coupler 66 can be permanently affixed together.

Figure 20A:
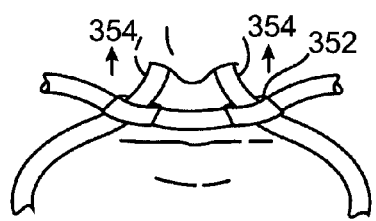
FIGS. 20A and 20B show front views of the head strap of FIGS. 19A and 19B.
Figure 20B:
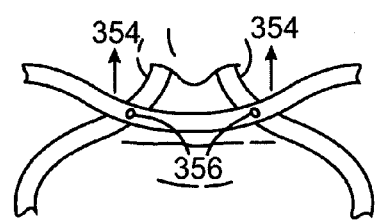

Alternatively, as shown in FIGS. 20A and 20B, the first strap 74 can include a slot 352 through which the distal ends of the interface tubes 32 pass (FIG. 20A), or a quick connect connection 356 to the interface tubes 32 (FIG. 20B), in order to provide additional lifting of the interface tubes lateral to the nose 354 to facilitate and maintain positive engagement with the nostril for sealing and overall apparatus retention. These attachment means may be floating attachments allowing some degree of motion between the interface tubes and the strap or may be non-floating. It can be appreciated that while certain specific aspects of the strap are disclosed, its uniqueness of lifting the distal tips against the nose for maintaining seal compression can be provided with a variety of attachment sites, fastening designs, and strap materials. In addition, the construction of the first strap 74 can include a shape memory or a shapeable member 75 to facilitate positioning and security of the device without sacrificing comfort.

FIG. 19B also shows a further embodiment of the present invention in which a nose or tilt pad 68 is located under the nose to tilt the angle 362 of the distal end of the interface tubes 32, relative to the face, so as to align the angle 160 of the interface tubing distal tip 235 with the angle of the nostril canals 162 in the Sagittal plane. The pad 360 preferably comprises a soft, deformable material such as a jell or a shape memory energy absorptive material such as a viscoelastic foam.

The tilt pad 68 can be attachable to the coupler 66 and or to the pair of interface tubes 32 directly under the nose and the attachment location is preferably keyed to assure proper orientation when connecting to create the upward lift 342 in the desired vector.

The nose or tilt pad 68 is preferably formed of a malleable material with an adherent surface, which is placed over the nose and shaped into a shape that prevents over-distention of the nostrils from the pressure being extended upward on the nostrils by the nasal interface. Alternatively, ear loops or a head strap can retain the tilt pad 68.

Alternatively, a variety of tilt pad sizes can be available to the user to select the correct tilt setting, or the tilt pad 68 itself can be adjustable. It can be appreciated that the tilt pad 68 can be an integral part of the coupler 66, the head strap connector 76, interface tubes or sealing cushions 46, or the tilt pad 68 and head strap connector 76 can connect to each other around or through the coupler 66. It can be appreciated that the pad can be attached to the head strap connector with a hinge such that the two snap together around the coupler.

Figure 21A:
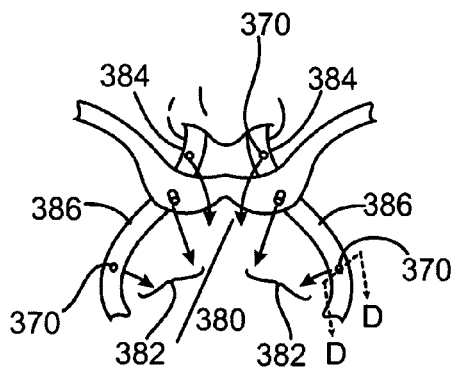
FIGS. 21A and 21B show a front and side view of exhaust vent ports angulated to be co-linear with the natural directional vector of exhaled gas.
Figure 21B:
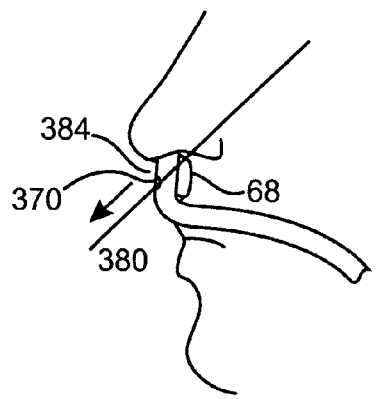

FIGS. 21A and 21B show a front and side view, respectively of another aspect of the present invention comprising ventilation exhaust vent ports 370. The exhaust vent ports 370 are generally used in a CPAP or VPAP patient interface applications since these systems do not include exhalation valves. The vent ports 370 lower the $CO_2$ levels inside the interface tubes 32 of the device 30, thus facilitate exhalation. In addition, the vent ports 370 provide a safety access to ambient air in the case of a gas source supply interruption.

As shown in FIGS. 21A and 21B, the vent ports 370 are configured in a diagonal orientation 380 with respect to the user's face so as to create a flow direction 382 outward from the face and downward from the nose, thus simulating the natural direction of nasal exhaled flow and directing the flow away from the user's face and not in the direction of the bed partner. The vent ports 370 can be located in the interface tubes 32 directly below the nose 384, or further proximally near the cheek 386.

Figure 22:
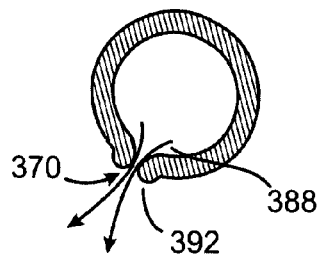
FIG. 22 shows a cross-sectional view of the exhaust vent ports of FIGS. 21A and 21B.

In a preferred embodiment, as shown in FIG. 22, the vent ports 370 are further configured for proper flow dynamics and entry effects (e.g., a chamfered or rounded leading edge 388) and there may be filtering for noise abatement (e.g., a low flow resistance filter integrated into the vent ports). The wall in the interface tubes 32 can be thickened 392 in the area to facilitate proper configuration and performance of the channels. It can be appreciated that the device 30 can be devoid of the vent ports 370 when used for PAP applications in which there is an exhalation valve in the tubing circuit.

Figure 23A:
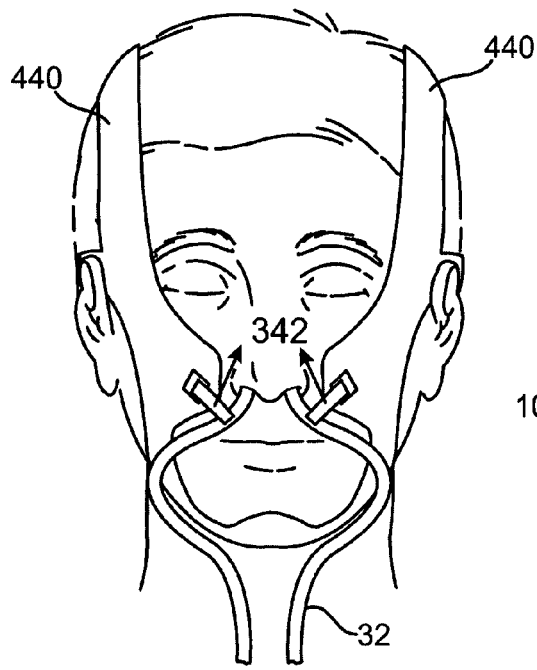
FIGS. 23A and 23B show a front and side view of a mandibular lift headband.
Figure 23B:
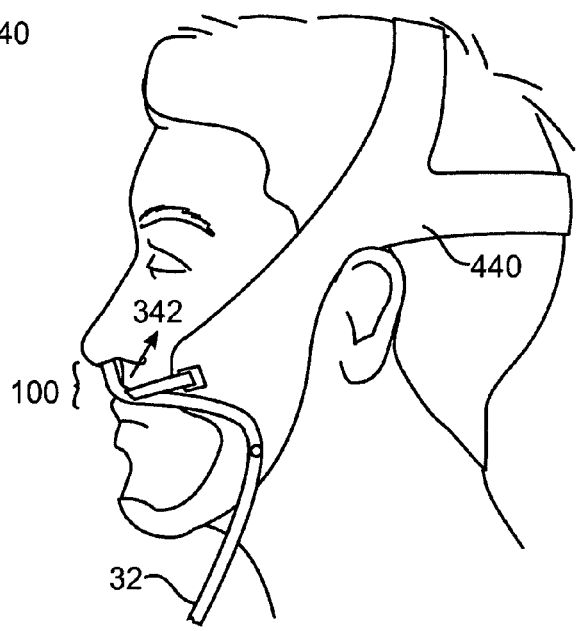

FIGS. 23A and 23B show a front and side view, respectively of a headband 440. The headband is configured to secure the interface tubes 32 in place while preventing the mandible 442 from opening in order to prevent mouth leaks. The headband 440 positions the distal end 100 of the interface tubes 32 to provide an upward lifting force 342 on'the interface tube distal tips 100 such that the tips are compressed against the nostril to maintain a seal. The headband 440 can be an adjustable design to meet a variety of anatomies, or can be available in a variety of sizes. The headband is preferably comprised of an elastomeric of stretchable foam type material such as neoprene.

In another embodiment, a conduit or tube can be integrated into the interface tubes 32 of the device 30 for the purpose of supplying supplemental oxygen concurrent with the PAP therapy. Alternatively, the conduits or tube can be integrated into the interface tubes 32 of the device 30, which are connected to a vacuum source for the purpose of scavenging CO2 rich air within the tubes 32 of the device 30. As shown in FIG. 36s A and B mouth shield 800 with a soft extension 802 can be used, which is interconnected to the device 30 and placed in the mouth for the purpose of blocking inadvertent leakage out of the mouth of the PAP air. It can be appreciated as shown in FIG. 37 that a therapeutic compound or relaxing aromatic scent can be injected into the ventilation gas supply, preferably be inserting a cartridge 810 into a receptacle 812 in-line with the device's ventilation supply tubing 64.

It can be appreciated that the nasal interface device 30 as shown in FIGS. 1-23 can comprise any, some or all of the described embodiments. Also, while most of the embodiments described relate to long term or repeated use of the device, such as with OSA, it can be appreciated that there are non-OSA ventilation uses that would also benefit from these embodiments, such as PAP therapy for COPD, anesthesia recovery, mechanical ventilator weaning, outpatient surgery use, and emergency ventilation. Further, it should be appreciated that in addition to CPAP or VPAP ventilation, the invention can be used for other forms of mechanical ventilation such as CMV, SIMV, etc. Finally it should be appreciated that with the necessary modifications, the device can be reusable or disposable and can be adapted for adult, pediatric or neonatal use.

Figure 24:
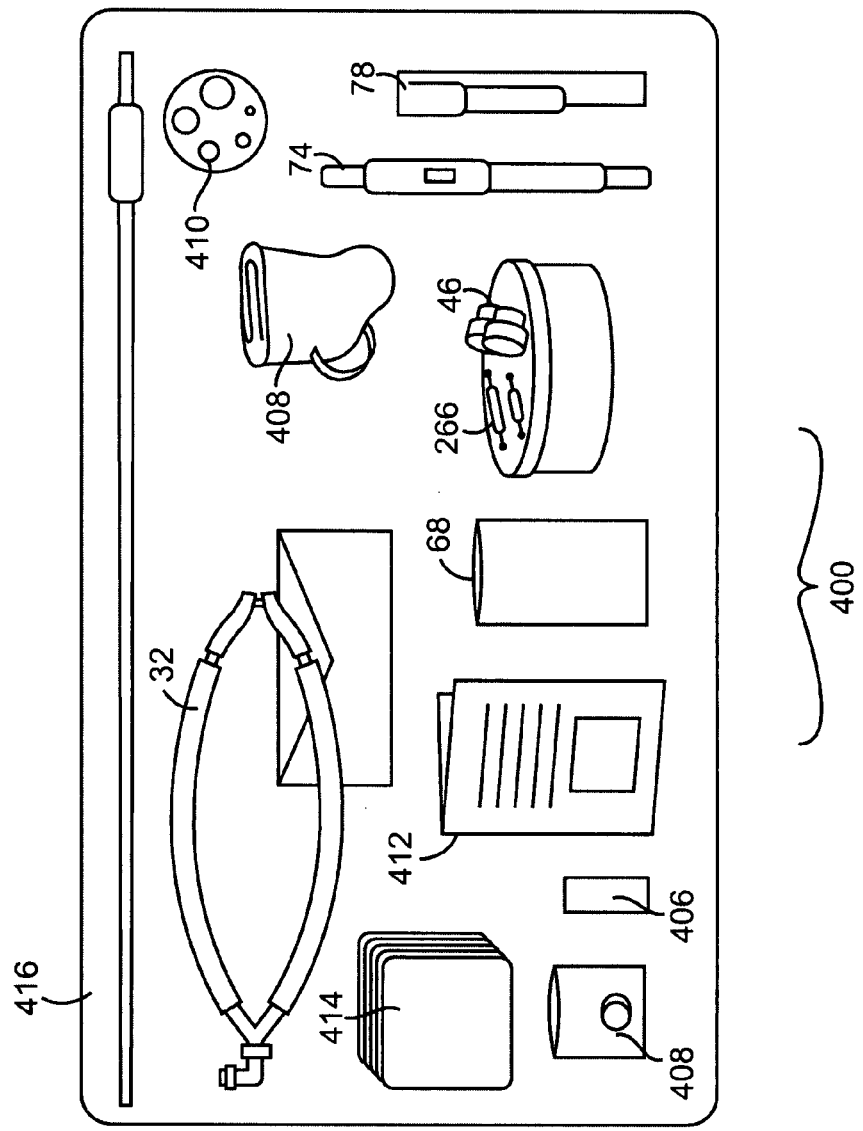
FIG. 24 shows a plan view of a nasal interface kit.

FIG. 24 shows a nasal interface kit 400 comprising a pair of nostril sealing cushions 46, a pair of interface tubes 32, a coupler 66, a first strap 74, a spare coupler 266, tilt pads 68, a second strap 78, a cleaning and storage container 404, skin ointment 406, aroma therapy cartridges 408, a sizing gage 410, instruction sheet 412, an interface storage bag 414, a chin/mouth closure head band 418, and a package 416 for the individual components.

Nasal Mask Interface

Figure 25:
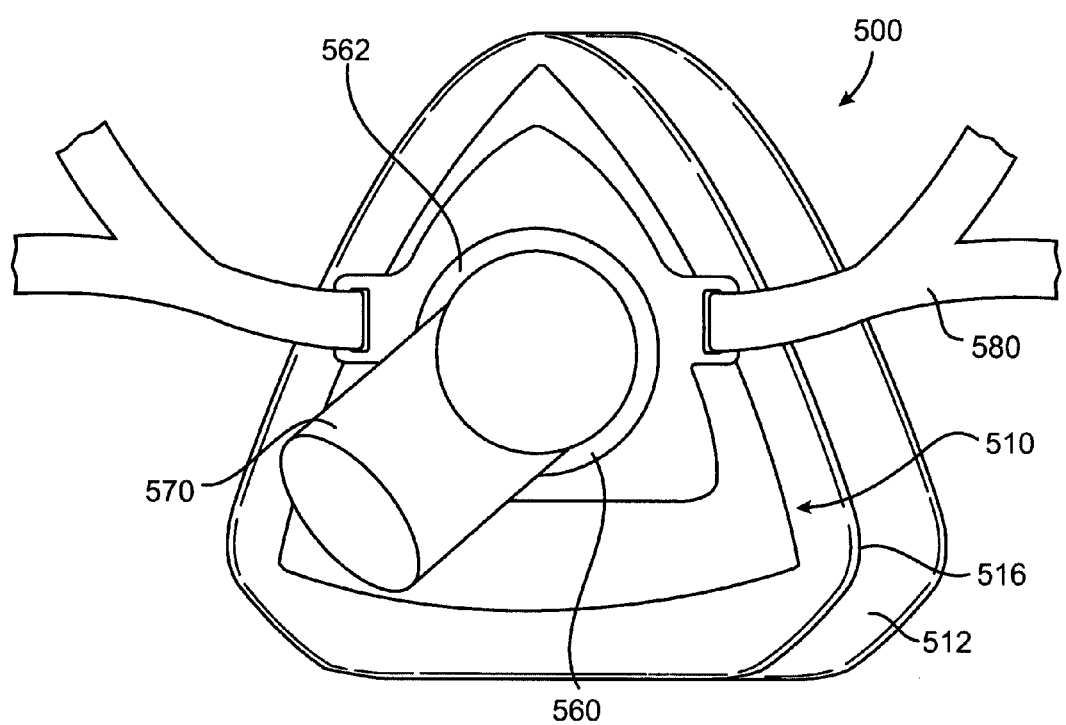
FIG. 25 shows a perspective view of a nasal mask for use with a ventilation system.

FIG. 25 shows a perspective view of a nasal mask 500 for use with a CPAP or VPAP ventilation system. The mask is preferably triangular shaped with a plastic concave shell 510 and a seal 512 extending around the perimeter on the concave side (for contacting the face). The seal 512 is preferably a shape-memory compressible foam member, which is attachable to a posterior or skin side of the shell 510 (as shown in FIGS. 26A-26I) of the mask's plastic concave shell 510. The shape-memory compressible foam member can be either permanently or removably attached to the posterior or skin side of the shell 510.

The seal 512 is generally a strip of approximately ⅜" to approximately 11" wide, and approximately ½" to approximately 1⅖" in height extending around the perimeter 516 of the generally triangular shell 510. It can be appreciated that the face side of the seal 512 is generally a planar surface; however, it can comprise undulations and curvatures matching the general anatomy of the nares or surrounding structures.

Preferably, the foam member of the seal 512 is a viscoelastic foam with a shape memory that is compressibly deformable such that the foam material can be compressed against the face without the material extruding, bending or flexing in directions normal to or diagonal to the compression direction.

The compressibility (and volumetric reduction) of the foam (without extruding sideways) truly allows the seal 512 to compressibly deform to match exactly the contours of the face around the nose. The energy absorptive properties of the foam allow the compressive forces to dissipate and spread somewhat evenly throughout the foam, such that areas requiring more compression (e.g., due to a high point in the facial anatomy) do not require elevated pressure to be exerted at that location. The same approximate pressure is exerted on the skin regardless of a recess or a protrusion in the anatomy.

Figure 26A:
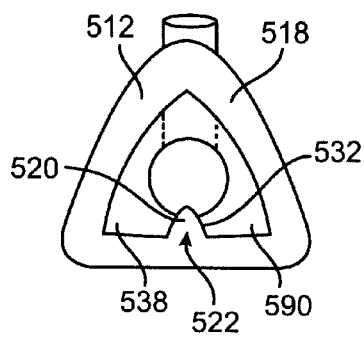
FIGS. 26A-26I show cross-sectional views of a nasal spacer positioned with the nasal mask of FIG. 25.

The foam surface 518 (as shown in FIG. 26A) can optionally be coated, encapsulated or covered (either completely or at certain locations) with a highly compliant elastomeric membrane for the purpose of hygienically controlling contaminants from entering the foam matrix or for facilitating cleaning of the foam surface.

Preferably, the surface pores of the foam at certain areas can be sealed with a compliant sealing substance, or the foam surface can be treated with an antimicrobial coating, or other coatings such as creams or hydrophobic, static, or bacteriostatic coatings or the like.

FIGS. 26A-26I show perspective views of a nasal spacer 520 positioned within the inferior or lower wall 522 of the foam seal 512. The nasal spacer 520 is positioned away from the opening of the nares to prevent nostril occlusion if the mask 500 were to shift during use.

Figure 26B:
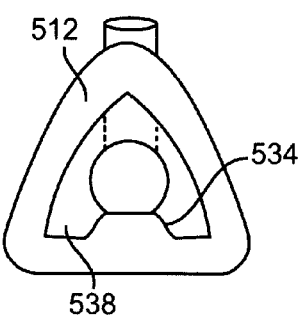
Figure 26C:
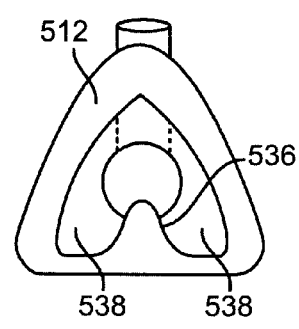
Figure 26D:
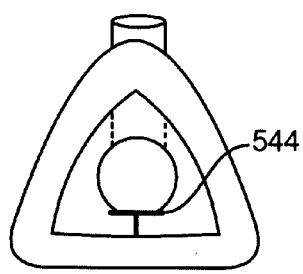
Figure 26E:
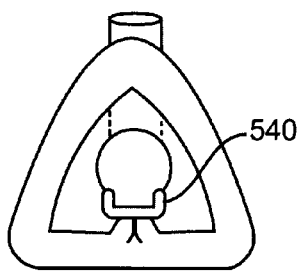
Figure 26F:
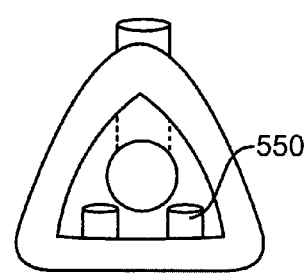
Figure 26G:
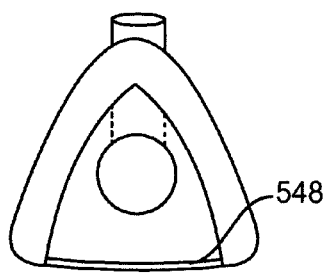
Figure 26H:
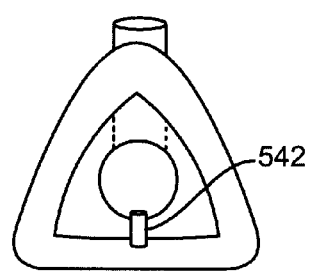
Figure 26I:
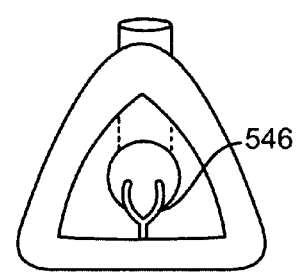
Figure 27A:
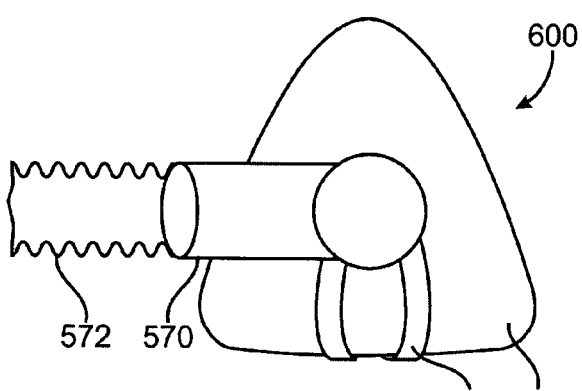
FIG. 27A shows a front view of a hybrid ventilation interface device comprising a nasal mask and a pair of interface tubes.
Figure 27B:
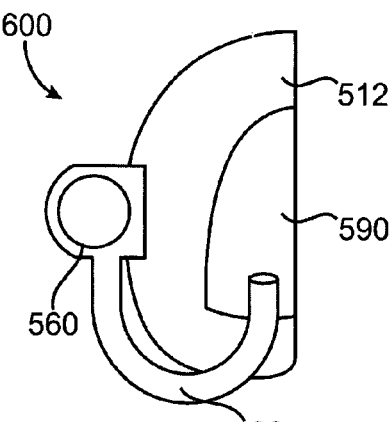
FIG. 27B shows a cross-sectional view of the of the hybrid ventilation interface device of FIG. 27A.
Figure 28A:
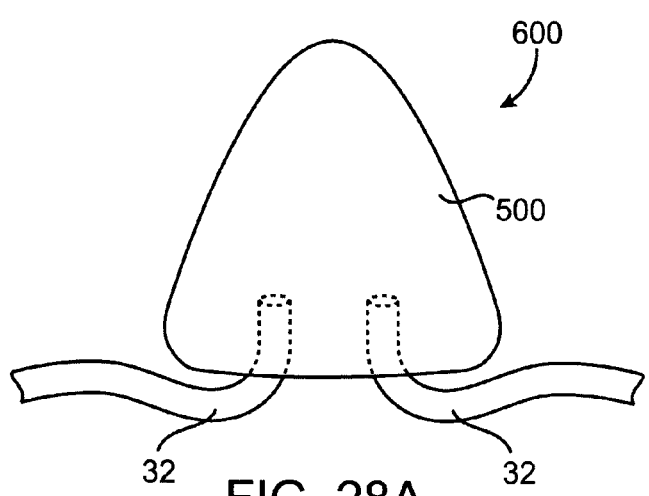
FIG. 28A shows a front view of another embodiment of a hybrid ventilation interface device.
Figure 28B:
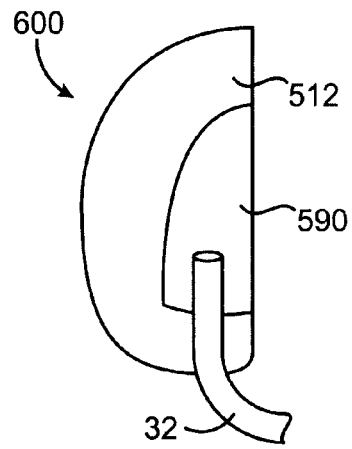
FIG. 28B shows a cross-sectional view of FIG. 28A.
Figure 29A:
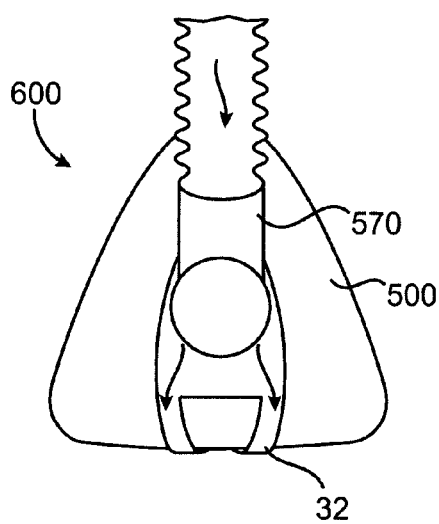
FIG. 29A shows a front view of a further embodiment of a hybrid ventilation interface device.
Figure 29B:
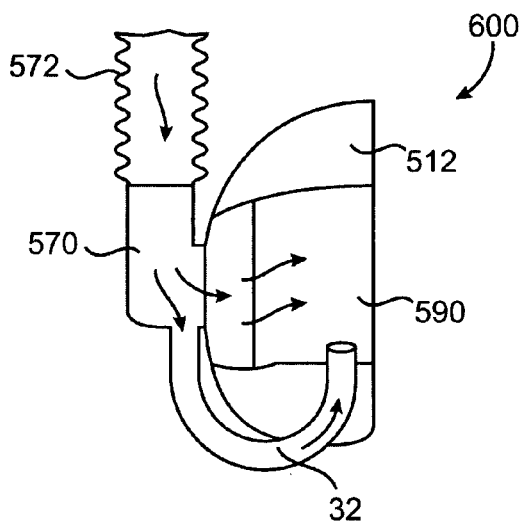
FIG. 29B shows a cross-sectional view of FIG. 29A.

As shown in FIGS. 26A-26I, the nasal spacer 520 can be of a variety of forms, such as (1) a soft compliant Y-shaped or U-shaped prong 530 extending superiorly from the inferior wall for hooking the nostril septum (FIG. 26E); (2) a superiorly extended boss 532, 534, 536 in the medial region of the seal's inferior wall continuous with the seal material (FIGS. 26A, 26B and 26C, respectively); (3) pockets or reliefs 538 in both lateral sides of the seal's inferior wall corresponding to the nostril locations (FIGS. 26A, 26B and 26C); (4) fenestrated 550 (FIG. 26F) or perforated nostril stand-offs 540 (FIG. 26E); (5) a spacer element 542 extending from the mask shell (FIG. 26H); (6) a T-shaped cross bar 544 (FIG. 26G); (7) a spring memory or malleable shapeable nostril septum clip 546 (FIG. 26I); (8) an elastomeric wall 548 defining the inferior seal rather than a foam material (FIG. 26G).

On the convex anterior side of the plastic shell a connector 560 is located, preferably an elbow swivel connector 562, for the purpose of attaching the mask 500 to a tubing 570 connectable to the gas pressure source. Fastening the mask 500 to the face can be performed with conventional strap systems 580 or can be performed with a headband 440 as shown in FIGS. 23A and 23B.

Routing of the breathing circuit tubing can be performed conventionally or can be performed with interconnect tubing 570 (FIG. 25) between the mask 500 and the breathing circuit connector (not shown) which is connected to a neck band.

In an alternative embodiment, a separate vacuum line can be applied to the concave side of the mask shell, thus applying vacuum to that volume when the mask is worn so as to assist in exhalation exhausting, $CO_2$ gas scavenging, enhancing the mask-face seal, or providing active exhalation. The mask's seal area preferably includes an integral exhaust ports extending through the body of the seal 512; the ports may have to be protected from collapse and pinching when the seal is compressed which is preferably accomplished by a pinch-resistant tube extending through the seal width. It can be appreciated that the nasal mask can comprises any, some or all of the described features.

Hybrid Nasal Interface Tubes-Mask Interface

FIGS. 27A, 27B, 28A, 28B, 29A, and 29B show a front and side view, respectively of three (3) ventilation interface devices 600. The devices 600 comprise (1) a mask 500 configured to seal around a portion of the nose including the rim of the nostril or nares; and (2) a pair of nasal interface tubes 32 configured to seal the nostrils. The interface tubes preferably comprise a distal tip 235 configured to seal the nostril. The interface tubes 32 can further include a pair of sealing cushions 46. The hybrid ventilation interface device 600 can be one of the preferred apparatuses or devices for the OSA CPAP user.

As shown in FIGS. 28A, 28B, 29A and 29B, the interface tubes 32 and the mask 500 cavity are both pressurized and are thus both connected to a gas pressure source, either independently or by utilizing the same tubing and connectors. The mask 500 portion can be relatively small compared to conventional masks because there is no worry about the mask edges occluding the nostrils since the nostrils are sealed with the interface tubes 32 hence assuring air delivery into the nose. The mask portion of the assembly secures the nasal interface tubes 32 in place and also provides a seal 510 on the face surrounding the nares.

The seal 512 can be performed with either the nasal interface tubes 32 with a nostril seal or sealing cushions 46, the mask perimeter facial seal 512, or both which can reduce unintended leaks. In this embodiment, when the system 600 is pressurized, the area outside the nares (inside the mask) is pressurized coincident with the inside of the nostrils being pressurized (via the interface tubes), hence there will be an pressure equilibrium between the inside and outside of the nose, thus helping to prevent leaks that occur due to pressurized dilation of the nostrils during CPAP.

In a typical nasal interface system, there is a pressure differential between the nasal cavity 590 (which is elevated positive pressure during CPAP inspiration) and outside the nose (which is ambient pressure) allowing the nostrils to dilate which encourages leakage. In the hybrid system 600, the trans-nasal-wall pressure is equalized.

In a further embodiment, the mask cavity 590 volume can be pressurized during an inspiratory cycle and depressurized during an expiratory cycle, so as to provide easier exhalation effort.

Alternately, the mask cavity 590 volume can be attached to a constant or semi-constant vacuum signal so as to help remove $CO_2$ build up in the overall system 600 or to synchronized to reduce exhalation effort. Alternately, a lower constant pressure level can be applied to the mask cavity 590 volume and a higher constant pressure level applied to the nasal interface tubes 32 with the intention that the interface tubes 32 will seal in the nostrils during inspiration but not exhalation (for example by nasal prong cuff inflation during the inspiratory cycle) thus allowing gas to escape easier during exhalation.

Alternatively only one nostril can be cannulated and/or sealed with a sealing cushion 46 from an interface tubes 32 with a NIT which is substantially sealed in the nostril and through this cannula or tube 32, the nasal cavity is pressurized to the therapeutic pressure level (preferably constantly but optionally intermittently) while the mask's cavity 590 outside the nares is pressurized to a lower exhalation pressure, thus facilitating and easing the work of exhalation out of the non-cannulated nostril. In this embodiment, it can be appreciated that there are a range of combinations, such as cycling pressure in the mask cavity 590 synchronously with the breathing cycle such that during inspiration the open nostril receives positive pressure gas from the mask cavity 590 to prevent flow escapage, but during exhalation the open nostril can receive lower pressure or even negative pressure to encourage exhalation flow.

Alternatively, the side of the nose being cannulated, sealed with a sealing cushion 46 and/or used to delivery inspired flow can be alternated throughout the night, for instance in response to nasal resistance shifting from one side to the other. In other aspects of this hybrid mask 600 embodiment, the mask 500 portion of the interface is not pressurized at all.

In these embodiments, the mask shell 510 and/or the interface tubes 32 includes the requisite exhalation exhaust vent fenestrations as is common with conventional interfaces, or can include some or all of the unique exhalation exhaust mechanisms described elsewhere in this disclosure. It can be appreciated that the hybrid interface tubes/mask 600 can include any, some or all of the described features as set forth herein.

Ventilation Interface Head Fasteners

FIGS. 3, 19A and 19B show a method and device for fastening or securing a ventilation interface device 30 to a user's face in a manner comfortable to the user and convenient to wear and remove. The fastening is accomplished with two general methods: (1) with straps 74, 78 that have integral malleable shapeable members 75 that can be shaped by the user and re-shaped repeatedly, or (2) straps 74, 78 that possess spring behavior or shape memory. FIGS. 19A and 19B show a shapeable fastener or strap comprising a malleable member 75. Once shaped into a desired shape, the material within the fastener or strap 74, 78 possess enough strength and deformation resistance to resist inadvertent shape changes.

The malleable fastener assembly can possess several different configurations for attaching to the head. As shown in FIGS. 19A and 19B, the fastener or strap assembly 74, 78 can be two bilateral extensions extending posteriorly from the ventilation interface device 30 wherein the user shapes the extensions to intimately contact the head as desired.

Alternatively, as shown in FIGS. 19A and 19B, the fasteners or straps 74, 78 can be bilateral extensions as already described however with straps attached at their posterior ends wherein the straps can be joined and cinched together at the rear of the head to secure the assembly in place. The fastener or strap 74, 78 can be an upward extension from the interface device 30 extending over the top of the head and down the back of the head toward the neck. In this configuration, the portion at the front of the head (between the eyes) may be very flat and low profile to the skin allowing the user to wear eyeglasses over the fastener.

The fastener or strap 74, 78 can comprise a quick connect feature on at least one end for quick and easy fastening to the interface device at or near the nose and/or at the back of the head, ears or neck band (described in subsequent sections).

Alternatively, the fastener or strap 74, 78 can be fixed to the interface device at one end and attachable at the other end, or a fastener can be fixed to the interface device 30 at one end fastened to something else (neckband, ear, or another fastener) at the opposite end.

The fastener or straps 74, 78 are preferably comprised of the malleable material preferably surrounded, encased, laminated or otherwise covered with a soft compliant material. The malleable material can be copper, nickel, brass or any other suitable material. The cross section of the fastener can be a wire or a plurality of wires, a strip with a flat rectangular cross section, or a round or oval cross section.

The outer covering is preferably a plastic (e.g., soft vinyl), an elastomer (e.g., rubber, synthetic rubber, silicone, and urethane), and a cushion type material (viscoelastic foam). The cushion aspects of the malleable material covering provide comfort and wear-ability of the fastener for the user. The malleable material and the covering can be joined at their interface to make the materials inseparable and behave in unison or can be loosely associated at their interface to allow relative motion between the two materials.

Another embodiment described in FIGS. 19A and 19B is a configuration wherein the malleable member is integral to the interface tubes 32, thus creating giving the interface tubes 32 the added function of a fastener or strap 74, 78.

Another embodiment of the interface fastener or strap 74, 78 is a configuration comprised of both the malleable member and an elastic strip wherein the malleable member is loosely attached to an elastic strip such that the elastic provides stretching and elastic tensioning of the fastener, but at the same time the malleable member provides rigidity of the fastener so it stays in the desired position and shape. The member or members can be attached to the elastic band for example by being sewn into or onto the elastic band, or can be attached to an elastic band by several fabric loops through which the strip is placed.

FIGS. 19A and 19B show one of the preferable embodiments of the spring memory fastener or strap 74, 78. As shown in FIGS. 19A and 19B, the fastener or strap 74, 78 comprises the same types of extension configurations, connections and padding as previously described. It can be appreciated that the fasteners or straps 74, 78 preferably incorporate mixture of features disclosed above can combine flexibility, softness, rigidity where needed, and shapeability.

Ventilation Interface Tubing Securement

FIGS. 3, 19A and 19B also show a method and device for routing and securing the gas delivery tubing for the ventilation interface device 30 in a manner that reduces the obtrusiveness and inconvenience to the conscious user. Specifically, the fastening method and device comprises (1) a second strap 78 in the form of a neckband that is attached to the neck and made of a soft compliant and optionally stretchable material, and easily fastenable onto the neck such as with Velcro, (2) an interconnect connector or bifurcation device 61 comprising a T, Y, and/or elbow swivel connector at the anterior aspect of the neck (e.g., attached to the neckband) with a machine end port and a patient end port, and (3) an interconnect tubing or supply gas hose 64 that connects the ventilation interface device 30, nasal mask 500, or hybrid system 600 to the patient end of the interconnect connector or bifurcation device 61. Tubing leading to the gas pressure source is attached to the machine end of the interconnect connector.

The interconnect connector or bifurcation device 61 is fixed to the second strap 78 or neckband and a second connector 60 (usually an elbow double swivel connector 60, 62) is attachable to the neckband interconnect connector. The interconnect tubes 32 are routed away from the interface device 30 (nose or mouth) to the second strap 78 or neckband in a variety of orientations: (1) either to the rear of the head or neck and then routed along the neck band to the anteriorly located interconnect connector, or (2) to the side of the neck where it is fastened to the neck band and then routed to the interconnect connector, or (3) routed downward from the interface directly to the interconnect connector on the front of the neck band, or (4) routed upward from the interface over the top of the head and down the back of the head to the rear of the neck band, then routed along the neck band to the located interconnect connector.

Figure 32:
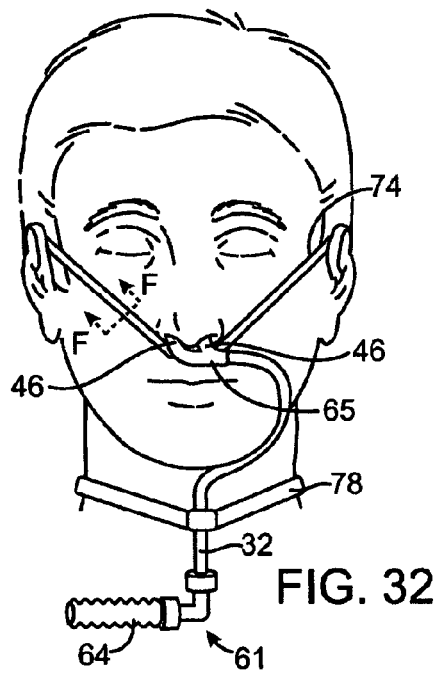
FIG. 32 shows a front view of an alternative embodiment of the nasal interface device.

The interconnect tubing can be two symmetric tubes on either side of the face, head and/or neck as shown in FIGS. 3, or can be a single tube as shown in FIG. 32. The section of the interconnect tubing fastened to the second strap 78 can be two symmetric sections of the interface tubes 32, or can be a single tube on one side of the neck as shown in FIG. 32.

In an optional embodiment, the tubing can itself perform the function of a neckband eliminating the need for a separate strap or neckband. A section of the interconnect tubing is preferably a flexible and stretchable (such as a corrugated-walled or ridged tube) to allow kink-resistant flexion in response to head and neck movement such that the interconnect tubing is not inadvertently disconnected on either end.

Part of the interconnect tubing can be fastened to the neckband to help secure it in place. Alternatively, the padding can surround part of the interconnect tubing especially if the interconnect tubing is routed to the back of the head or neck or the face to make it comfortable to the user.

It can be appreciated that the tubing routing and fastening systems serve to control the position of tubing so as to direct it away from, for example, the patient's senses (nose, mouth, eyes or ears) in a desirable orientation that is less obtrusive. The tubing can thus be directed away from the users senses or field of vision, thus allowing for more freedom of activities, making it easier to move, and also minimizing the sensation of having one's face tethered to the gas source with a large tube.

In addition to the neckband interconnect arrangements just described, other optional tubing securement and routing systems can be used to accomplish the same objective. For example one alternative configuration is an interconnect connector attached to the lapel area or chest area of a user's night shirt, for example with a grasping clip, or ear lobe clips, thus accomplishing the same objective but without the need for a neck band.

Ventilation Exhaust and Venting

FIGS. 21A, 21B and 21C show an exhalation flow and $CO_2$ blow-off exhaust ports device. As discussed, exhaust ports 370 are preferably a requirement in conventional OSA CPAP interfaces (nasal masks and nasal interface tubes) whereas they are not required in non-CPAP ventilation because non-CPAP ventilation systems include a separate exhalation valve in the system. In the present invention, five different types of exhaust systems are disclosed; (1) angulated fenestrations axially angulated in the direction of exhaled flow, (2) an exhaust intake scoop, (3) a directional flapper valve, (4) a directional sleeve valve, and (5) a vacuum assisted exhaust port.

FIGS. 21A and 21B show angulated fenestrations, which are placed in the wall of the nasal interface tubes 32 at or near the base of the sealing cushions 46 (i.e., located outside of the nostrils below the nose). The fenestrations or vent ports 370 are preferably placed at a diagonal angle 380 so as to direct the air in a downward (inferior) and outward (forward or anterior) direction 382 so that the exhaust flow direction simulates that of air normally being exhaled from the nose. This minimizes annoyance to the user and bed partner. The angulated fenestrations or vent ports 370 have the added benefit of biasing the degree of flow resistance such that resistance is low when flow inside the interface tubes 32 is in the exhaled direction and high when flow inside the interface tubes is in the inhaled direction, because the entrance of to the channels from inside the interface tubes are generally parallel with the direction of exhaled flow, but at 180° angles to the direction of inspired flow. Thus, the angulated fenestrations or vent ports 370 increase the exhaust leak in the "vacuum assisted exhaust systems."

The vacuum exhaust is preferably created by a separate vacuum line with a distal end communicating with the lumen of the breathing circuit tube at a location somewhat at or near the patient interface (nasal mask or nasal interface tubes) and a proximal end connected to a vacuum generating source. A constant or intermittent vacuum is applied to remove CO rich gas. Preferably, the vacuum can be created by a retrograde (reverse direction) positive pressure jet airflow, which will entrain air to escape with it (i.e., a venturi effect). However, the exhaust system vacuum can be constant, intermittent and/or timed with the breathing cycle (e.g., on during exhalation phase and off during inspiration phase). In the venturi system, the venturi pressure source and the ventilation gas pressure source can be the same source or different sources.

Portable PGU 700

Figure 30:
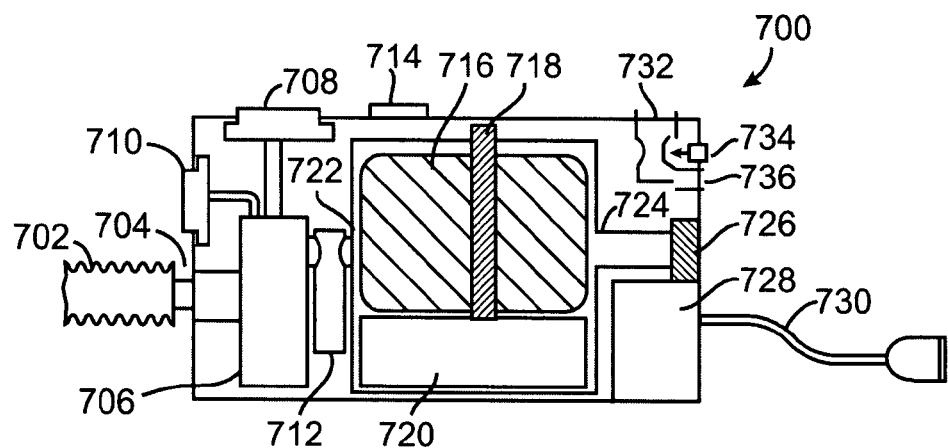
FIG. 30 shows a front view of a portable breathing gas pressure generating and delivery unit.
Figure 31:
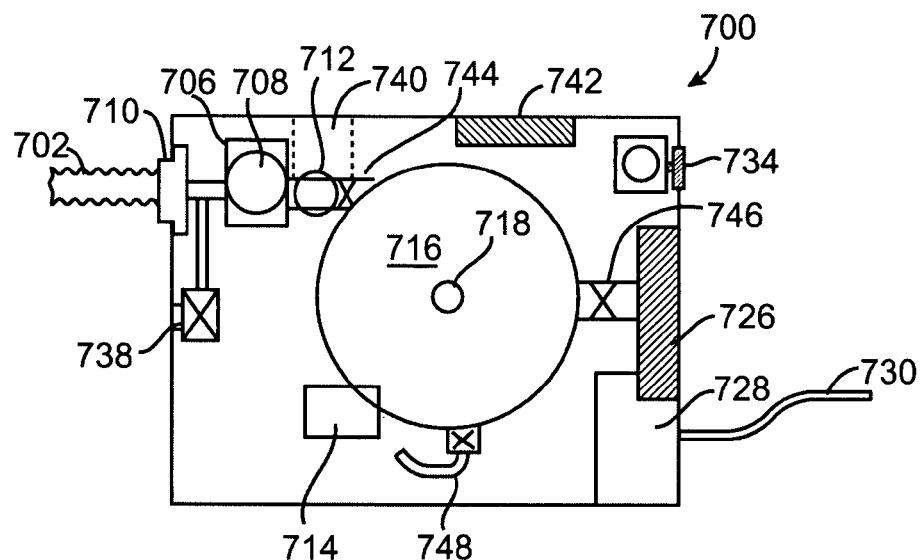
FIG. 31 shows a top view of the portable breathing gas pressure generating and delivery unit of FIG. 30.

FIGS. 30 and 31 shows a portable breathing gas pressure generating and delivery unit 700 (PGU), which is designed to be compact and portable for travel purposes.

Typically, the conventional PGU's for CPAP and BiPAP applications have a variable speed motor to control a variable speed air blower fan (ABF) and the requisite digital electronics and microprocessors, analog electronics, sensors and software to control the speed of the motor. The user sets the prescribed therapeutic pressure level and the ABF speed is automatically adjusted as necessary compensating for the prevailing conditions (tubing resistance, etc.) to achieve that pressure.

In the present invention the ABF is not automatically adjusted and instead the user sets the speed of the motor/ABF manually until the desired pressure output is achieved. The motor control electronics can thus be made less inexpensive and possibly smaller for more compactness.

As shown in FIGS. 30 and 31, the portable breathing gas pressure generating and delivery unit comprises a gas supply hose 702, a gas outlet tubing connector 704, a pressure regulator 706, a regulator adjustment 708, a pressure gauge 710, a moisture trap 712, a motor and fan speed selector switch 714, a fan and blower 716, a fan and blower shaft 718, a fan and blower motor 720, a fan and blower gas outlet 722, a fan and blower gas inlet 724, replaceable HEPA filter 726, a power supply module 728 comprising a rechargeable battery, transformer, fuse and other related components, a power cord 730 for either AC or 12V DC current; an adjustable airway resistance simulator 732 and breathing circuit 734 configured such that the user can adjust the pressure output; an airway resistance simulator adjustment device 736 configured to allow the user to adjust selected high and low resistance, a airway resistance gas outlet 738, an exhalation exhaust flapper valve 740, an access compartment for accessing the moisture trap 742, a filter, air inlet and outlet 744 configured to cool the device, a blower fan outlet check valve 746, a blower fan inlet check valve 748, a blower fan bleed to cool the inside of the unit including the motor or blower fan and/or auxiliary inlet to obtain warm air from the motor heat into the blower and thus entraining into a gas delivered to the use to warm the gas 750, a rubberized surface 752 and a sliding door to protect the controls and connections 754.

In a second embodiment of the portable PGU 700, a new manner of calibrating the pressure output of the PGU 700 to the individual user is described. To facilitate proper pressure output setting, the PGU 700 includes an airway resistance simulator test port 756. The user attaches the distal end of the breathing circuit tube or gas supply hose 702 to the test port 756 while setting the pressure setting. The resistance simulator has several settings to properly simulate the resistance of the individual's airway or the degree of their airway obstruction. For example, if the individual has a very high critical opening pressure of their airway, they would set the simulator setting to maximum and in contrast an individual with a low critical opening pressure of their airway would set the simulator setting to minimum. The simulator settings would be for example 1-5, 5 being highest. This way the pressure output is set with the correct resistance in place.

In a third embodiment of the portable PGU 700, optional pressure generating mechanisms are described. Besides the conventional rotary vane blower and fan 716 for generating pressure, the pressure can be generated by (1) a fan with a concentric motor, (2) a piston pump, (3) a turbine, (4) a centrifugal pump, (5) a gear pump, (6) a rotary piston pump, (7) an impeller pump, or (8) an dual action piston pump with the same direction output on both strokes by the use of valves. Also, besides generating flow with the conventional single pump systems, there can be an array of small pumps, preferably in parallel, so as to create greater flow output in a smaller overall size, or to alternate between pumps where the pump outputs are non-continuous as in a piston pump.

In a forth embodiment of the portable PGU 700 to further facilitate portability, the unit can be powered with a non-120 Volt AC power source, such as a 12 Volt DC power source (with an internal battery, an external battery or cigarette lighter power cord) and is equipped accordingly. Additionally the unit 700 can be equipped with a charging system, for example a chargeable power storage device (e.g., battery, capacitor) connectable to a power source such as a transformer and/or 120/240 Volt AC supply and/or DC supply. The charging system input power can be attached with a simple conventional connector or can be a docking station. Or the chargeable power storage unit can be modular and replaceable into the PGU 700 and charged outside of the unit 700. Further, the charging of the power storage unit can be a manually charging system, such as a manual wind-up system.

In a fifth embodiment of the portable PGU 700, the air being delivered to the patient can be conditioned in a variety of manners, such as moisturizing and warming. Warming can be accomplished by collecting warm air that is generated from the ABF or pump motor and inputting it into the ABF, or by channeling the ABF air output past the motor to warm the air. Moisturization can be accomplished by including a low resistance filter in the ABF air outlet path wherein the filter can be wetted by the user so that the air collects moisture on the way to the patient. Further, the moisturizer can be warmed by warm air that is collected from the ABF motor, or alternately can be warmed by a peltier element. In these embodiments the ABF motor is also prevented from overheating do to the bleeding off of heat.

In a sixth embodiment of the portable PGU 700, the unit 700 may also include an exhalation valve (for example a directional flapper valve) that leaks to atmosphere during exhalation but which is sealed to atmosphere during inspiration. The valve is preferably included near the air outlet of the PGU 700.

In a further embodiment of the portable PGU 700, the unit is constructed with flush mounted, recessed mounted or cover-protected dials, gauges, connectors and controls to avoid damage to it. This facilitates reliability and robustness of the unit for traveling use.

In another embodiment of the portable PGU 700, the unit enclosure is ruggedized, for example by using polymer or rubber construction of the enclosure, or by surrounding the enclosure with rubber or polymer protection. The PGU 700 can also include a corrugated air hose that can be compressed from its full length of 6'-8' to 1' to facilitate portability. The PGU 700 can also bleed off room temperature air in the ABF to cool the inside of the PGU 700 to prevent overheating. The PGU 700 can be super-insulated for noise dissipation and abatement.

It can be appreciated that the PGU 700 comprises all the requisite regulators, valves, sensors, gauges, conduits, electric wiring, analog and digital electronics. The purpose of these novel features is to provide a portable PGU 700 that is extremely low cost and small footprint such that travelers can easily travel with the equipment and perhaps own a dedicated travel PGU 700 rather than traveling with their heavier more expensive PGU 700. A typical user would be a frequent traveler such as a sales representative, persons taking overseas flights frequently, or a truck driver who can keep the PGU 700 in the truck and use it with 12 VDC. It should be noted that any and all of these embodiments can be combined or mixed as needed.

It can be appreciated that while the various embodiments described are especially useful for OSA CPAP applications, they are also useful for other non-OSA and non-CPAP applications such as emergency, NIV, COPD, weaning from IMV, or the like.

Alternative Aspects of the Nasal Interface Device

FIG. 32 shows a front view of an alternative embodiment of the nasal interface device 30. As shown in FIG. 32, the device comprises a gas supply hose 64, a hose coupler 61, a tube 32 and a bifurcated nasal cushion 65. The nasal cushion 65 comprises a first end configured to attach to the tube 32 and a second end configured to receive a pair of sealing cushions 46. Alternatively, the second end of the nasal cushion 65 can be designed with the sealing cushions 46 fixed to the second end of the nasal cushion 65.

The nasal cushion 65 is preferably designed to avoid the turbulent flow associated with the base manifold 20 as shown in FIGS. 1 and 2 by incorporating gradual curves or arcuate design into the nasal cushion 65. Preferably, the nasal cushion 65 comprises a pair of lumens 69 configured to deliver a ventilation gas to the nostril of the user. The lumens 69 preferably do not have any 90 degree angles and provide a smooth and arcuate configuration for laminar flow.

The device 30 is secured to the user with a first strap 74 (headband) and a second strap 78 (neckband). As shown in FIG. 32, the device 30 is secured to the neck and then is positioned on or around the jaw of the user. It can be appreciated that the device 30 can be positioned on or around the jaw of the user from either side (FIGS. 32 and 33A) of the face to allow the wear to sleep more comfortably on one side or the other. Alternatively, the tube 32 can be an over the head tube configuration secured to the user by known methods of over the head style nasal interface cannulae and devices as shown in FIG. 33B.

Figure 34:
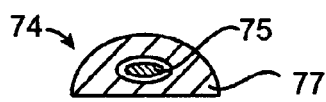
FIG. 34 shows a cross sectional view of a strap of FIG. 32 along line F-F.

FIG. 34 shows a cross-section of a first strap 74 or a second strap 78 taken along the line F-F of FIG. 32. As shown in FIG. 34, the first strap 74 or second strap 78 comprises a malleable material 75 preferably surrounded, encased, laminated or otherwise covered with an outer material 77 of a soft compliant nature. The malleable material 75 can be copper, nickel, brass or any other suitable material. Alternatively, the malleable material 75 as shown in FIG. 34 can be a wire or a plurality of wires, a strip with a flat rectangular cross section, or a round or oval cross section.

The outer material 77 is preferably comprises of a plastic (e.g., soft vinyl), an elastomer (e.g., rubber, synthetic rubber, silicone, and urethane), or a cushion type material (viscoelastic foam). The cushion aspects of the outer material 77 provide comfort and wearability of the straps 74, 78 for the user. The malleable material 75 and the outer material 77 can be joined at their interface to make the materials inseparable and behave in unison or can be loosely associated at their interface to allow relative motion between the two materials.

The first strap 74 and the second strap 78 are preferably fastened behind the head and/or neck by a Velcro system 174, 178, respectively. However, it can be appreciated that other methods of connecting the ends of the straps 74, 78 can be implemented without departing from the invention.

Figure 33A:
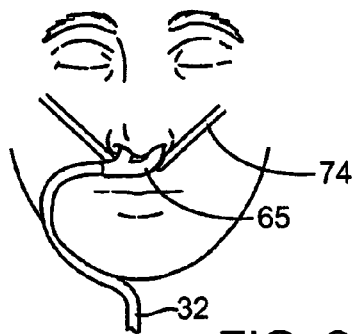
FIG. 33A show a front view of a further embodiment of the nasal interface device of FIG. 32.
Figure 33B:
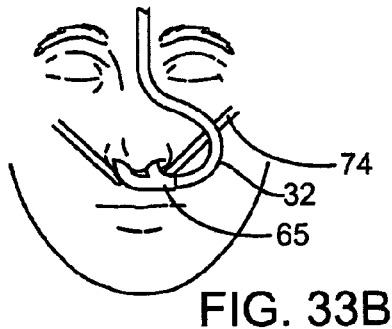
FIG. 33B shows a front view of another embodiment of the nasal interface device of FIG. 32.
Figure 35:
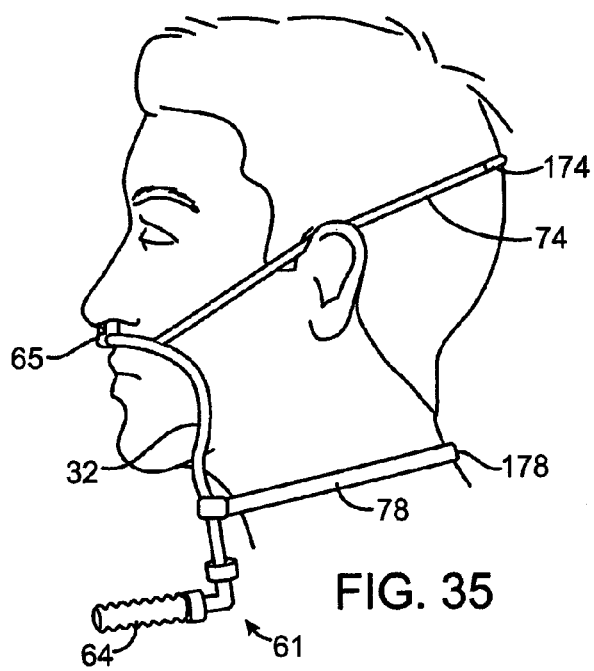
FIG. 35 shows a side view of the nasal device of FIG. 32 showing how the device hugs the face for comfort.

FIG. 35 shows a side view of the nasal interface device of FIGS. 32, 33A and 33B. As shown in FIG. 35, the device 30 is designed to fit closely and hug the face of the user. The close fit and hugging nature of the device 30 provides for as much comfort as possible.

It can be appreciated that the tubes 32 can also include a shape memory material. The shape memory material is created by a preformed shape or by a shape memory member which is integral to at least a portion of the tubing.

The nasal device as shown in FIGS. 3A and 4 have been tested for both air flow resistance and estimated noise production. Table 1 is a sample of those test results.

TABLE 1

Air Flow Resistance (cm $H_2O$ vs. LPM)

|  | 30 | 50 | 80 |
|---|---|---|---|
| Conventional Device #1 | | | |
| XS (size) | 0.5 | 1.3 | 3.1 |
| S | 0.5 | 1.1 | 2.6 |
| L | 0.4 | 1.0 | 2.0 |
| XL | 0.4 | 1.0 | 1.8 |
| Conventional Device #2 | | | |
| X (size) | 0.2 | 0.5 | 1.3 |
| S | 0.2 | 0.5 | 1.1 |
| M | 0.2 | 0.5 | 1.1 |
| X | 0.2 | 0.5 | 1.1 |
| Conventional Device #3 | | | |
|  | 0.2 | 0.4 | 1.0 |
| Nasal Device as Shown in FIGS. 3A and 4 | | | |
| S (size) | 0.2 | 0.3 | 0.9 |

Noise Production (db's at 50 LPM - estimated at a 2 to 3 foot distance from the device)

| Device #1 | 45.0 |
|---|---|
| Device #2 | 50.0 |
| Device #3 | not available |
| Nasal Device | 42.0 |

As shown by the test results in Table 1, the nasal interface device 30 as shown in FIGS. 3A and 4 provides for reduced air flow resistance as a result of the laminar flow of the device which delivers the ventilation gas without turbulent flow as known in the prior art. Furthermore, the reduced air flow resistance provides reduced noise production.

Figure 36A:
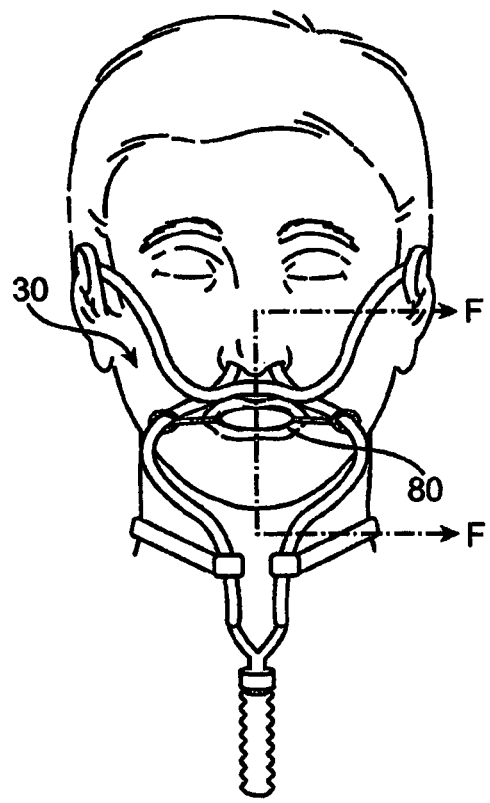
FIG. 36A shows a front view of a mouth guard according to one embodiment of the present invention.
Figure 36B:
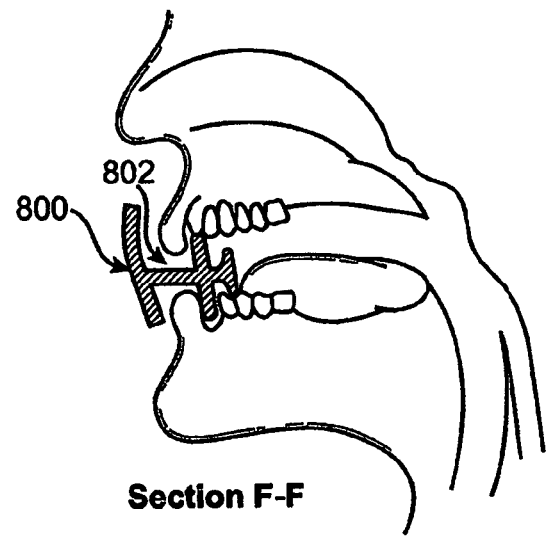
FIG. 36B shows a cross-sectional view of the mouth guard of FIG. 36A along the line F-F.
Figure 37:
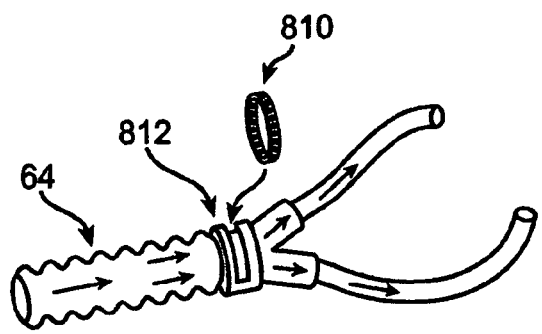
FIG. 37 shows a perspective view of an aromatherapy delivery technique.

FIGS. 36A and 36B describe an alternate embodiment that includes a mouth shield 80, 800 that helps prevent leakage of ventilation gas out of the mouth in the event the user is a mouth breather. The shield is a highly compliant structure that fits between the lips and teeth and on the outside of the mouth shield can be attached to the cannula tubing. The shield can include a posterior protrusion 802 that extends behind the front teeth to facilitate retention in the mouth.

FIG. 37 describes an optional embodiment in which aroma therapy is provided to calm a user (or other therapeutic uses) by means of a reservoir or cartridge release system 810 that releases aroma molecules inline 812 into the ventilation gas supply. Optionally, the aroma therapy can be provided by simply applying the solution to the cannula apparatus, for example, while washing.

While the invention has been described in detail with reference to the preferred embodiments thereof, it will be apparent to one skilled in the art that various changes and modifications can be made and equivalents employed, without departing from the present invention.

What is claimed is:

1. A nasal ventilation interface comprising;
a pair of tubes for providing ventilation including,
 a distal section of the pair of tubes configured to be engagable with a person's nostrils,
 a proximal section attachable to a ventilation gas supply, and
 a midsection of the pair of tubes configured for connecting the distal and proximal sections;
wherein the distal section pair of tubes comprise:
 (a) compound arcuate curves which are configured such that the distal section of the pair of tubes are adapted to extend from the nostril downward around the corners of the mouth to the chin and which are substantially stabilized in a performed configuration to stabilize and position the compound arcuate curves around the corners of the mouth and chin,
 (b) the compound arcuate curves are configured such that the pair of tubes are adapted to curve such that the distal section of the pair of tubes is adapted to be in substantial contact with the skin and are substantially stabilized in a performed configuration to stabilize and position the compound arcuate curves substantially in contact with the skin and resist malformation of the configuration of the curves,
 (c) and a coupling element interconnecting the pair of tubes that is adapted to be positioned between the nostrils and upper lip wherein the coupling element comprises a length adjuster.

2. The interface of claim 1, wherein an absence of abrupt angles within the tubes provides for laminar flow of the ventilation gas.

3. The interface of claim 1, further comprising a sealing cushion configured to be attachable to said distal section pair of tubes and configured to impinge the rim of the nostril.

4. The interface of claim 3, wherein the sealing cushion further comprises a step, wherein the step provides a seal on the rim of the nostril and prevents the sealing cushion from extending beyond a desired depth into the nostril.

5. The interface of claim 1, wherein said coupling element and said distal end section tubes are joined together by a swivel means, said swivel means configured to adjust and align the angle of the distal end of the distal end section with the angle of the nostrils.

6. The interface of claim 1, wherein the skin side of the coupler further comprises a facial pad, the facial pad configured to allow for angular adjustment of the distal end of the distal section pair of tubes to angularly align with the angle of the nostrils in the sagital plane.

7. The interface of claim 6, further comprising a first strap, wherein the first strap is attachable to the bottom side of the coupler beneath the nose and in the center of the face.

8. The interface of claim 7, wherein the first strap extends laterally over the ears providing upward lift directly beneath the nose.

9. A nasal ventilation interface comprising:
a distal end configured to engage a user's nostrils;
a proximal end configured to attach to a ventilation gas supply; and
a mid-section between the proximal and distal ends, wherein the distal end and the mid-section comprises a pair of tubes having an arcuate non-angulated shape and having an absence of pneumatic interconnections between each of the tubes of the pair,
the tubes comprising a first curved section at the distal end adapted to curve downward and laterally from the user's nostrils toward the corner of the mouth, a second curved section adapted to curve laterally, posteriorly and downward around the corner of the mouth toward a mandible between an anterior and a posterior aspect of the mandible, and a third curved section adapted to curve downward and medially to the anterior aspect of the neck and further wherein the tubing in at least one of the curved sections is positioned against the user's skin and wherein the first, second and third curved sections are substantially stabilized in a preformed configuration adapted to secure the first, second and third curved sections in substantial contact with the skin and resist malformation of the first, second and third curved sections away from the skin.

10. The interface of claim 9, further comprising a coupler connecting said distal end pair of tubes together, said coupler comprising: (a) a swivel joint at the attachments to said distal tubes, and (b) a length adjustment.

11. The interface of claim 9, wherein the mid-section is routed around the back of the user's neck.

12. The interface of claim 9, wherein the distal end is pre-formed into a curved tubular shape, wherein the shape comprises three sections, a first generally straight distal portion, a second generally curved portion which extends downward, outward and backward, and a third proximal portion which is curved downward, wherein the curves place the proximal end of the distal end tubing section generally lateral to the corners of the user's mouth.

13. The interface of claim 9, wherein a portion of the distal section of tubing has a non-circular, flat cross-sectional profile, and wherein a wider section of the profile is against placed the user's skin.

14. The interface of claim 9, further comprising a mouth shield, wherein the mouth shield is attachable to the pair of tubes and configured to be placed at least partially in the mouth to control air flow exiting the mouth.

15. The interface of claim 14, wherein the mouth shield further comprises a compliant flat section for insertion into the mouth of the user.

16. The interface of claim 9, further comprising at least one lumen in a wall of the pair of tubes, wherein the lumen is attached to a source of supplemental oxygen.

17. The interface of claim 9, further comprising exhaust vent ports, wherein the ports are comprised of fenestrations in the wall of the pair of tubes, and wherein the fenestrations are angulated diagonally outward or laterally from the nose.

18. The interface of claim 9, further comprising a receptacle for receiving a therapeutic compound, wherein the ventilation gas picks up and conducts molecules of the compound to the user's nose with the ventilation gas.

19. A nasal ventilation interface comprising:
a pair of tubes having at a distal end configured to engage a user's nostrils and a proximal end configured to attach to a manifold;
a single tube including a proximal end configured to attach to a ventilation gas supply, and a distal end configured to attach to the manifold, wherein the single tube is configured to extend unidirectionally away from the nostrils to one side of the face and a distal section of the single tube comprises:
(a) compound arcuate curves which are configured to extend from the manifold downward around the corner of the mouth to the chin and is substantially stabilized in a performed configuration to stabilize and position the curves around the corner of the mouth and chin,
(b) the compound arcuate curves are configured such that the single tube is adapted to curve such that the distal section is adapted to be in substantial contact with the skin and is substantially stabilized in a performed configuration adapted to stabilize and position the curves substantially in contact with the skin and resist malformation of the curves.

20. The interface of claim 19, further comprising a sealing cushion configured to be attachable to the distal section and configured to impinge a rim of the nostril.

21. The interface of claim 20, wherein the sealing cushion further comprises a step, wherein the step is adapted to provide a seal on the rim of the nostril and prevents the sealing cushion from extending beyond a desired depth into the nostril.

22. The interface of claim 19, wherein a skin side of the manifold further comprises a facial pad, the facial pad configured to allow for angular adjustment of the distal end of the distal section of the tube to angularly align with the angle of the nostrils in the sagital plane.

\* \* \* \* \*